United States Patent
Nakamitsu

(10) Patent No.: US 12,089,816 B2
(45) Date of Patent: Sep. 17, 2024

(54) ENDOSCOPE INSERTION SHAPE OBSERVATION APPARATUS AND MANUAL COMPRESSION POSITION DISPLAY METHOD

(71) Applicant: OLYMPUS CORPORATION, Tokyo (JP)

(72) Inventor: Takechiyo Nakamitsu, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 804 days.

(21) Appl. No.: 17/206,478

(22) Filed: Mar. 19, 2021

(65) Prior Publication Data
US 2021/0205026 A1    Jul. 8, 2021

Related U.S. Application Data

(63) Continuation of application No. PCT/JP2018/034682, filed on Sep. 19, 2018.

(51) Int. Cl.
*A61B 5/00* (2006.01)
*A61B 1/00* (2006.01)
(Continued)

(52) U.S. Cl.
CPC .......... *A61B 1/0051* (2013.01); *A61B 1/0005* (2013.01); *A61B 1/00147* (2013.01);
(Continued)

(58) Field of Classification Search
CPC .............. A61B 1/009; A61B 2034/107; A61B 2034/102; A61B 1/0051
See application file for complete search history.

(56) References Cited

U.S. PATENT DOCUMENTS

2011/0098533 A1* 4/2011 Onoda ................. A61B 1/0051
                                                              600/117
2018/0177383 A1* 6/2018 Noonan ............... A61B 1/0051
(Continued)

FOREIGN PATENT DOCUMENTS

JP       2002172084 A       6/2002
JP       2006288752 A      10/2006
(Continued)

OTHER PUBLICATIONS

International Search Report dated Nov. 27, 2018 received in PCT/JP2018/034682.
(Continued)

*Primary Examiner* — Rajeev P Siripurapu
(74) *Attorney, Agent, or Firm* — Scully, Scott, Murphy & Presser, P.C.

(57) ABSTRACT

An endoscope insertion shape observation apparatus includes a processor, and the processor: detects a travelling direction of a first position detection member and a travelling direction of a second position detection member out of plural position detection members provided in an insertion portion inserted into a lumen of a subject, the first position detection member being provided on a distal end side of a bending portion of the insertion portion, the second position detection member being provided on a proximal end side of the bending portion; detects a stretch start timing in which the lumen starts stretching, based on detection results of the travelling directions and finds position coordinates of a predetermined position of the bending portion in the detected stretch start timing as a manual compression point; and causes a compression position display that indicates the position found as the manual compression point to be presented on a monitor.

12 Claims, 19 Drawing Sheets

(51) Int. Cl.
    *A61B 1/005*     (2006.01)
    *A61B 5/06*     (2006.01)
    *A61B 34/20*     (2016.01)
    *A61B 90/00*     (2016.01)

(52) U.S. Cl.
    CPC .............. *A61B 5/062* (2013.01); *A61B 34/20* (2016.02); *A61B 90/39* (2016.02); *A61B 1/009* (2022.02); *A61B 2034/2051* (2016.02); *A61B 2034/2055* (2016.02); *A61B 2090/3937* (2016.02); *A61B 2090/3983* (2016.02)

(56) References Cited

U.S. PATENT DOCUMENTS

2018/0263467 A1*   9/2018   Takahashi .............. A61B 1/009
2019/0239723 A1*   8/2019   Duindam ............. A61B 1/0016

FOREIGN PATENT DOCUMENTS

| | | | |
|---|---|---|---|
| JP | 2006314710 A | 11/2006 | |
| JP | 2006314711 A | 11/2006 | |
| JP | 2007044412 A | 2/2007 | |
| JP | 2016049353 A | 4/2016 | |

OTHER PUBLICATIONS

Takayoshi, et al., "Utilization of Endoscopic Insertion Form Observation Devices", vol. 28, No. 4, Apr. 25, 2016.
Partial English Translation only of Takayoshi, et al., "Utilization of Endoscopic Insertion Form Observation Devices", vol. 28, No. 4, Apr. 25, 2016 (previously cited in IDS filed Mar. 19, 2021).

\* cited by examiner

FIG. 3

| PROCEDURAL IMAGES | ENDOSCOPE INSERTION | INSERTION DIFFICULTY STATE | RETRACTION OF DISTAL END | MANUAL COMPRESSION OF ABDOMINAL WALL FIXING OF INTESTINAL TRACT | REINSERTION |

ENDOSCOPE INSERTION SHAPE OBSERVATION APPARATUS AND MANUAL COMPRESSION POSITION DISPLAY METHOD

CROSS REFERENCE TO RELATED APPLICATION

This application is a continuation application of PCT/JP2018/034682 filed on Sep. 19, 2018, the entire contents of which are incorporated herein by this reference.

BACKGROUND OF THE INVENTION

1. Field of the Invention

The present invention relates to an endoscope insertion shape observation apparatus used to observe an inserted state of an endoscope and a manual compression position display method.

2. Description of the Related Art

Conventionally, endoscope apparatuses have been used widely in a medical field. An endoscope apparatus is medical equipment having an elongated flexible insertion portion, and a surgeon can observe an interior of a subject by inserting the insertion portion into a body of the subject. An endoscopic image of the interior of the subject picked up by an endoscope can be displayed on a monitor. However, it is not possible to see from the endoscopic image how the endoscope insertion portion is inserted in the body of the subject.

Thus, as an apparatus that allows the inserted state of the endoscope to be seen during insertion of the endoscope, an endoscope insertion shape observation apparatus has been developed, which includes a receiving antenna and a monitor, where the receiving antenna is made up of a plurality of transmitter coils incorporated into an insertion portion and a plurality of sense coils placed in a coil block and the monitor displays an insertion shape of the insertion portion.

For example, in colonoscopy, a surgeon performs an operation of inserting the insertion portion into an intestinal tract while watching an endoscope insertion shape. However, part of the intestinal tract such as a sigmoid colon is not fixed by a retroperitoneum, and may move and stretch when the insertion portion is inserted. In such a part (hereinafter referred to as a stretchable part), it is difficult to insert the insertion portion. Thus, a manual compression method may be adopted, which assists in allowing the insertion portion to advance smoothly by compressing the stretching intestinal tract by hand from outside the body.

Note that Japanese Patent Application Laid-Open Publication No. 2006-314710 discloses a manual compression assistance system that can automatically compress a specific position indicated by a surgeon.

SUMMARY OF THE INVENTION

An endoscope insertion shape observation apparatus according to one aspect of the present invention includes a processor, and the processor: detects a travelling direction of a first position detection member and a travelling direction of a second position detection member out of a plurality of position detection members provided in an insertion portion inserted into a lumen of a subject, the first position detection member being provided on a distal end side of a bending portion of the insertion portion, the second position detection member being provided on a proximal end side of the bending portion; detects a stretch start timing in which the lumen starts stretching, based on detection results of the travelling directions and finds position coordinates of a predetermined position of the bending portion in the detected stretch start timing as a manual compression point; and causes a compression position display that indicates the position found as the manual compression point to be presented on a monitor.

A manual compression position display method according to one aspect of the present invention includes: detecting a travelling direction of a first position detection member and a travelling direction of a second position detection member out of a plurality of position detection members provided in an insertion portion inserted into a lumen of a subject, the first position detection member being provided on a distal end side of a bending portion of the insertion portion, the second position detection member being provided on a proximal end side of the bending portion; detecting a stretch start timing in which the lumen starts stretching, based on detection results of the travelling directions; calculating position coordinates of a predetermined position of the bending portion in the detected stretch start timing as a manual compression point; and causing a compression position display that indicates the position calculated as the manual compression point to be presented on a monitor.

BRIEF DESCRIPTION OF THE DRAWINGS

FIG. 3 is an explanatory diagram for illustrating a procedure for manual compression;

DETAILED DESCRIPTION OF THE PREFERRED EMBODIMENTS

Embodiments of the present invention will now be described in detail below with reference to the drawings.

First Embodiment

Figure 1:
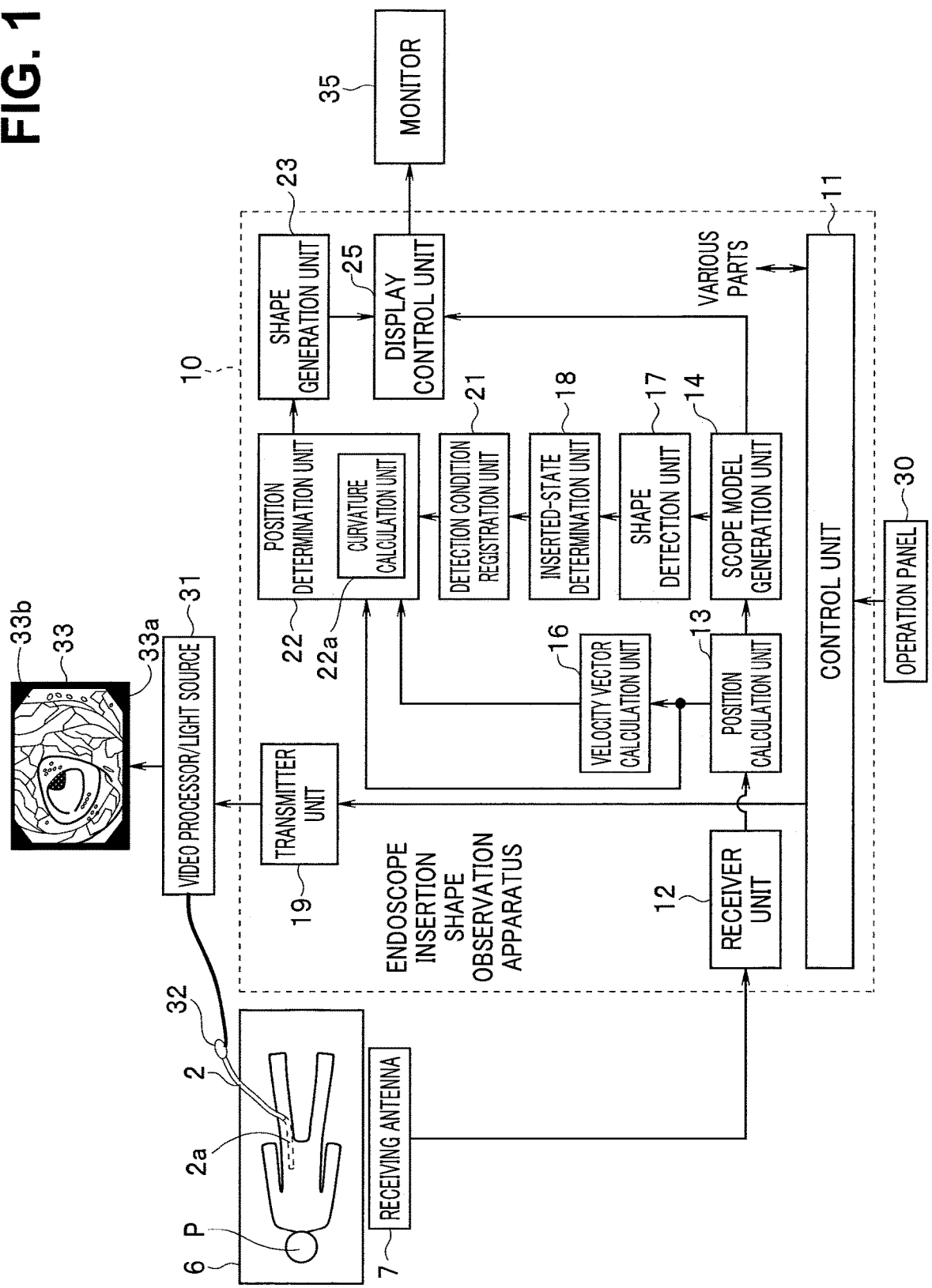
FIG. 1 is a block diagram showing an endoscope insertion shape observation apparatus according to a first embodiment of the present invention.
Figure 2:
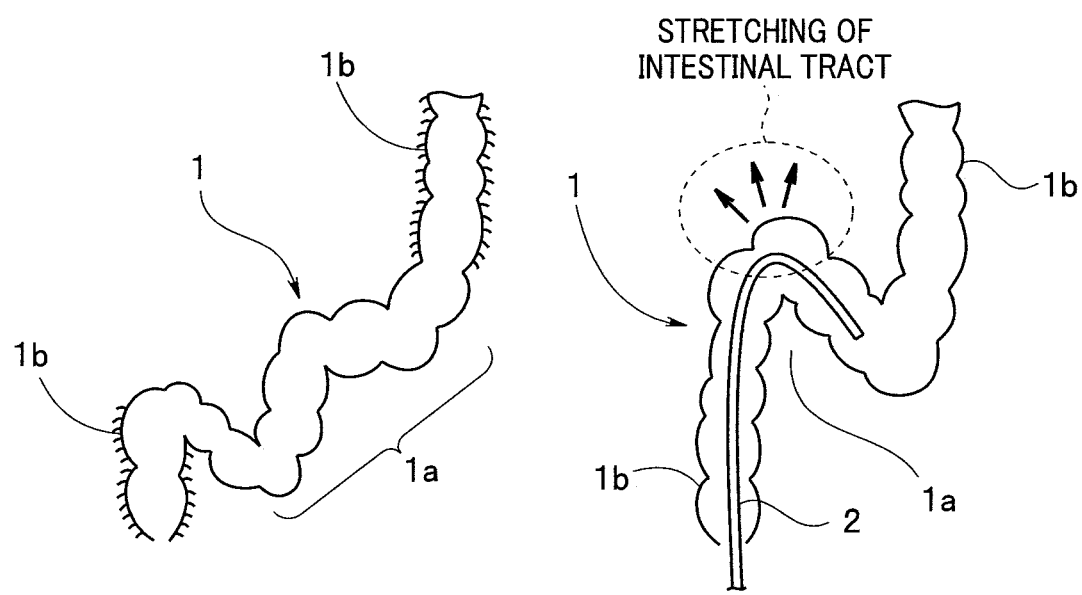
FIG. 2 is an explanatory diagram for illustrating a procedure for manual compression.

FIG. 1 is a block diagram showing an endoscope insertion shape observation apparatus according to a first embodiment of the present invention. FIGS. 2 and 3 are explanatory diagrams for illustrating procedures for manual compression.

The present embodiment displays an insertion shape image indicating an insertion shape of an endoscope as well as presents a display (hereinafter referred to as a compression position display) indicating a position to be manually compressed (hereinafter referred to as a manual compression point). By checking the compression position display, even a caregiver relatively inexperienced in caregiving can manually compress a necessary spot in a reliable manner.

First, a procedure for manual compression will be described with reference to FIGS. 2 and 3. FIG. 2, which is intended to explain stretching of the intestinal tract, which is a lumen, shows an intestinal tract 1 before insertion of an insertion portion 2 of the endoscope on the left side and the intestinal tract 1 after insertion of the insertion portion 2 of the endoscope on the right side. The intestinal tract 1 includes a part (hereinafter referred to as a fixed part) 1b fixed by a retroperitoneum that is not illustrated and a stretchable part 1a that is not fixed. The stretchable part 1a changes shape relatively greatly according to flexibility of the intestinal tract 1. Consequently, when the insertion portion 2 is inserted into the intestinal tract 1, the stretchable part 1a changes shape with changes in insertion direction and shape of the insertion portion 2. The right side of FIG. 2 shows how the insertion portion 2 is inserted into the intestinal tract 1 in the direction upward from the bottom of the paper. As the insertion portion 2 moves ahead in the stretchable part 1a, a travelling direction of the insertion portion 2 becomes different from a depth direction of the intestinal tract 1, and consequently the stretchable part 1a stretches in the direction indicated by the arrows under a pressing force of the insertion portion 2.

FIG. 3 shows states before and after manual compression in the procedure of inserting the insertion portion 2 into the intestinal tract 1. "Endoscope insertion" in FIG. 3 indicates that the insertion portion 2 is inserted into the intestinal tract 1. As the insertion portion 2 reaches the stretchable part 1a and moves further ahead, the stretchable part 1a stretches as described in FIG. 2, causing "insertion difficulty state." The insertion difficulty state (stretching of the intestinal tract) is a state in which the stretchable part 1a, which is stretchy, is being pushed in by a bending portion of the insertion portion 2, and it becomes difficult to insert the insertion portion 2. In this case, the surgeon retracts the insertion portion 2 once as shown in "retraction of distal end," and then attempts reinsertion.

During reinsertion, a caregiver carries out manual compression (manual compression of the abdominal wall) by hand 3, which involves compressing that portion of the stretchable part 1a in which stretching occurs, from outside the body. Consequently, shape of that portion of the intestinal tract 1 which corresponds to the stretchable part 1a is fixed, making it easy for the insertion portion 2 to move ahead in the stretchable part 1a, and the insertion portion 2 moves ahead smoothly in the depth direction of the intestinal tract 1 as a result of "reinsertion."

In this way, in inserting the insertion portion 2 into the intestinal tract 1, the manual compression is an extremely important procedure. However, as described above, is it not easy for a caregiver inexperienced in caregiving to recognize a manual compression point from outside the body. Note that it is conceivable to guess the manual compression point based on a display of an insertion shape. However, when the stretchable part 1a stretches, the surgeon retracts the insertion portion 2 once, making it necessary to constantly observe and memorize the display of the insertion shape and make a guess based on changes in the memorized shape, and thus it is not easy to guess the manual compression point.

Thus, according to the present embodiment, during insertion of the insertion portion 2 into the intestinal tract 1, a timing for the intestinal tract 1 to start stretching is sensed, a point at which the insertion portion 2 is bent most is detected with the sensed timing, thereby finding the manual compression point, and the manual compression point is displayed on a screen as a compression position display.

In FIG. 1, a subject P is lying on an examination bed 6, with the insertion portion 2 of an endoscope 32 inserted in the large intestine of the subject P through the anus. The endoscope 32 is connected with a video processor/light source 31. The video processor/light source 31 generates illuminating light for use to illuminate the subject. The illuminating light from the video processor/light source 31 is led to a distal end portion of the insertion portion 2 via a non-illustrated light guide passed through the insertion portion 2 of the endoscope 32 and is emitted at the subject from the distal end portion of the insertion portion 2.

A non-illustrated image pickup device is placed in the distal end portion of the insertion portion 2, being designed such that reflected light (return light) from the subject form an image as an optical image of the subject on a light-receiving surface of the image pickup device by being reflected off the subject. The image pickup device, driving of which is controlled by the video processor/light source 31, converts the optical image of the subject into an image signal, and outputs the image signal to the video processor/light source 31. The video processor/light source 31 includes a non-illustrated image signal processing unit, which receives an image signal from the image pickup device, performs signal processing, and outputs to a monitor 33 an endoscopic image resulting from the signal processing. Consequently, an endoscopic image 33b of the subject is displayed on a display screen 33a of the monitor 33 as shown in FIG. 1.

The bending portion is provided at a distal end of the insertion portion 2, being designed to be driven in a bendable manner via a non-illustrated bending knob provided in an operation portion of the endoscope 32. The surgeon can push the insertion portion 2 into the body cavity by bending the bending portion by operating the bending knob.

A plurality of transmitter coils 2a for use to observe inserted state of the insertion portion 2 are also provided in the insertion portion 2. The transmitter coils 2a serving as position detection members are arranged at predetermined intervals in an axial direction from the distal end of the insertion portion 2 and each of the transmitter coils 2a is driven by a signal from the video processor/light source 31. As described later, individual transmitter coils 2a are driven independently and generate respective magnetic fields. Note that a placement location of each transmitter coil 2a in the insertion portion 2 has been prescribed, and positions of the respective transmitter coils 2a with respect to a proximal end portion or the distal end portion of the insertion portion 2 are known.

A receiving antenna 7 is placed on a lateral side of the bed 6. The receiving antenna 7 includes a plurality of coil blocks that are not illustrated. Each of the coil blocks is made up, for example, of three sense coils wound in three directions such that coil surfaces intersect one another at right angles. For example, four coil blocks, that is, twelve sense coils, are arranged in the receiving antenna 7 as a whole. Each of the sense coils is designed to detect a signal proportional to magnetic field strength of an axial component orthogonal to the coil surface of the sense coil. For example, the coil blocks are designed to receive generated magnetic fields, convert the magnetic fields into voltage signals, and output the voltage signals as detection results. Each coil block and each transmitter coil 2a of the receiving antenna 7 have operating states controlled by an endoscope insertion shape observation apparatus 10.

As shown in FIG. 1, the endoscope insertion shape observation apparatus 10 is provided with a control unit 11. The control unit 11 may be made up of a processor that uses a CPU or the like and configured to operate based on a program stored in a non-illustrated memory. Alternatively, some or all functions of the control unit 11 may be implemented by electronic hardware circuits such as FPGAs. The control unit 11 controls the entire endoscope insertion shape observation apparatus 10. Note that illustrations of connections between the control unit 11 and various parts of the endoscope insertion shape observation apparatus 10 are omitted. The non-illustrated memory stores not only the program describing processes of the control unit 11, but also data and the like used in position calculations described later.

Note that not only the control unit 11, but also various components of the endoscope insertion shape observation apparatus 10 may be made up of a processor using a CPU and the like and configured to operate based on programs stored in the non-illustrated memory, thereby controlling various parts, or some or all functions may be implemented by electronic hardware circuits.

The control unit 11 controls a transmitter unit 19. The transmitter unit 19 is made up, for example, of a FPGA and designed to generate and output, for example, a sinusoidal signal for use to drive the transmitter coils 2a under the control of the control unit 11. Note that the sinusoidal signal is supplied to the transmitter coils 2a in the insertion portion 2 from the transmitter unit 19 via the video processor/light source 31. The transmitter unit 19 is designed to be able to supply a sinusoidal wave separately to the individual transmitter coils 2a under the control of the control unit 11. In other words, the control unit 11 can control which of the transmitter coils 2a is to be supplied with the sinusoidal wave.

When a high-frequency sinusoidal wave is applied, each transmitter coil 2a circumferentially emits an electromagnetic wave accompanied by a magnetic field. Note that the endoscope insertion shape observation apparatus 10 can drive the plurality of transmitter coils 2a in sequence at appropriate time intervals, e.g., at intervals of a few milliseconds. The endoscope insertion shape observation apparatus 10 can also individually specify timings in which the respective transmitter coils 2a generate magnetic fields.

Using the sense coils, the receiving antenna 7 receives the magnetic fields generated by the transmitter coils 2a and converts the magnetic fields into voltage signals. The receiving antenna 7 gives the voltage signals as detection results to a receiver unit 12 of the endoscope insertion shape observation apparatus 10. When being given the signals from the receiving antenna 7, the receiver unit 12 applies predetermined signal processing including an amplification process and then outputs the signals to a position calculation unit 13.

The position calculation unit 13, which is made up, for example, of a DSP, performs a frequency extraction process (Fourier transform: FFT) on inputted digital data, separates the digital data into pieces of magnetic field detection information on frequency components corresponding to the high-frequency sinusoidal waves of the respective transmitter coils 2a, extracts the magnetic field detection information, and calculates spatial position coordinates of the respective transmitter coils 2a from respective items of digital data on the separated magnetic field detection information. Calculation results of the position coordinates produced by the position calculation unit 13 are supplied to a scope model generation unit 14. The scope model generation unit 14 serving as an insertion shape image generation unit generate a linear image as an insertion shape image by connecting the position coordinates of the respective transmitter coils 2a.

The insertion shape image generated by the scope model generation unit 14 is given to a display control unit 25. The display control unit 25 is designed to generate display data for use to cause the insertion shape image generated by the scope model generation unit 14 to be displayed on the monitor 35 and output the display data to the monitor 35. The monitor 35, which can be made up, for example, of an LCD, displays the insertion shape image based on the display data, where the insertion shape image is based on relative positional relationship between the transmitter coils 2a and the receiving antenna 7.

The display data of the insertion shape image generated by the scope model generation unit 14 is generated using a coordinate system (hereinafter referred to as a measurement coordinate system) with respect to position of the antenna 7. The display control unit 25 performs coordinate transformation to cause the insertion shape image to be displayed at a predetermined position on a display screen of the monitor 35. In other words, the display control unit 25 performs coordinate transformation to transform the inputted display data from the measurement coordinate system to a display coordinate system. As a result of the coordinate transformation, the display control unit 25 can cause the insertion shape image to be displayed in a predetermined orientation and size at a predetermined position on the display screen of the monitor 35. The display position, orientation, and size of the insertion shape image can be changed by operation of the surgeon.

An operation panel 30 is designed to be able to accept user operation of the surgeon and the like and output an operation signal based on the user operation to the control unit 11. The operation panel 30 is designed to allow the surgeon to specify a size change and the like of the insertion shape image. The display control unit 25 is designed to change the size of the insertion shape image to be displayed on the monitor 35 when instructed to change the size of the insertion shape image from the control unit 11 based on the user operation.

Output of the position calculation unit 13 is also given to a velocity vector calculation unit 16 and output of the scope model generation unit 14 is also given to a shape detection unit 17. The velocity vector calculation unit 16 serving as a travelling direction detection unit is designed to calculate, based on the output of the position calculation unit 13, a velocity vector of the transmitter coil 2*a* (hereinafter referred to as the transmitter coil 2*an*) placed within a predetermined distance from the bending portion on a proximal end side of the bending portion out of the plurality of transmitter coils 2*a* placed in the insertion portion 2 and a velocity vector of the transmitter coil 2*a* (hereinafter referred to as the transmitter coil 2*a*1) placed at a distal end or on a distal end side of the bending portion out of the plurality of transmitter coils 2*a* placed in the insertion portion 2. The velocity vector calculation unit 16 outputs calculation results to a position determination unit 22.

The shape detection unit 17 is designed to be able to detect predetermined shapes of the insertion portion 2 in the body cavity based on the insertion shape image from the scope model generation unit 14. By adopting a known technique, the shape detection unit 17 can detect, for example, whether shape of the insertion portion 2 match any of linear, stick-like, looped, and other shapes. The shape detection unit 17 is designed to output information about the detected shape to a inserted-state determination unit 18. The inserted-state determination unit 18 determines whether the shape detected by the shape detection unit 17 is a predetermined shape such as a stick-like shape and outputs a determination result to a detection condition registration unit 21.

The detection condition registration unit 21 is designed such that conditions (detection conditions) for sensing the timing (stretch start timing) in which the intestinal tract 1 into which the insertion portion 2 is inserted starts stretching is registered in the detection condition registration unit 21. If the determination result produced by the inserted-state determination unit 18 indicates that the shape of the insertion portion 2 has become a predetermined shape that can cause the stretchable part 1*a* to stretch, the detection condition registration unit 21 outputs registered detection conditions to the position determination unit 22. Consequently, the position determination unit 22 starts detecting a stretch start timing based on the detection conditions.

Note that whereas in the example described above, the position determination unit 22 starts detecting a stretch start timing when the inserted-state determination unit 18 determines that the shape detection unit 17 has detected, for example, a stick-like shape, the position determination unit 22 may be designed to start detecting the stretch start timing when the shape detection unit 17 and the inserted-state determination unit 18 detect that a bent state of the bending portion of the insertion portion 2 has become a predetermined state. For example, the position determination unit 22 may be designed to start detecting the stretch start timing when the shape detection unit 17 and the inserted-state determination unit 18 detect a state in which an average value of curvatures of various parts of the bending portion is larger than a predetermined threshold, a state in which a maximum value of curvature of the bending portion is larger than a predetermined threshold, or a state in which curvature at a predetermined position of the bending portion is larger than a predetermined threshold.

Figure 4:
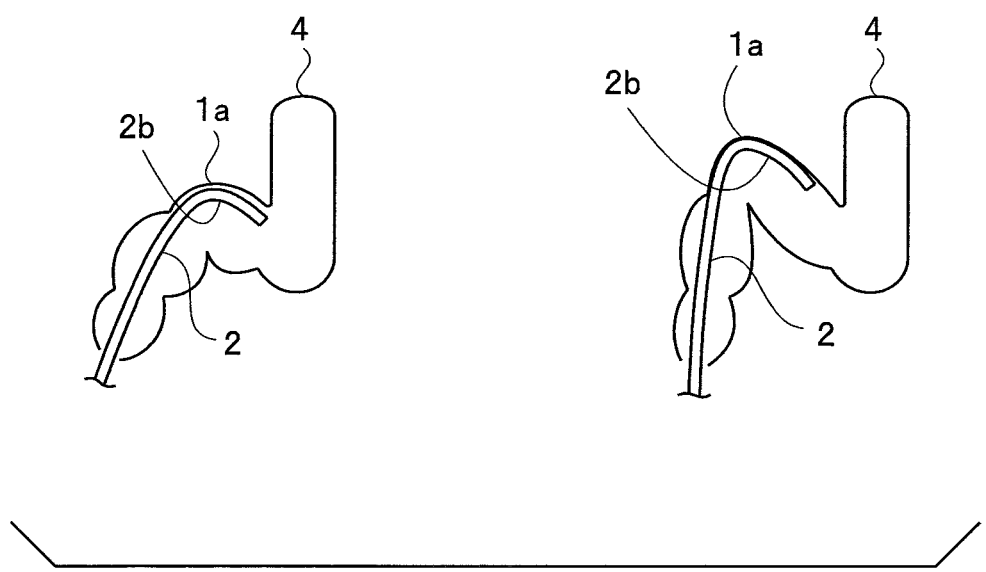
FIG. 4 is an explanatory diagram for illustrating a stretch start timing.

FIG. 4 is an explanatory diagram for illustrating a stretch start timing. The left side of FIG. 4 shows a state just before a stretch start timing. The insertion portion 2 is inserted in the intestinal tract 1 and a bending portion 2*b* at a distal end of the insertion portion 2 has reached the stretchable part 1*a*. When the insertion portion 2 is pushed in further, the stretchable part 1*a* starts stretching and then the stretchable part 1*a* becomes fully stretched as shown on the right side of FIG. 4. As shown in FIG. 4, it is considered that stretching of the intestinal tract 1 occurs when the insertion portion 2 assumes a stick-like shape. Thus, according to the present embodiment, the detection condition registration unit 21 is designed to output detection conditions to the position determination unit 22 when the inserted-state determination unit 18 detects a stick-like shape of the insertion portion 2.

The position determination unit 22 may be made up of a processor using a CPU and the like and configured to operate based on programs stored in the non-illustrated memory, thereby controlling various parts, or some or all functions may be implemented by electronic hardware circuits. The position determination unit 22 has been provided with the output of the position calculation unit 13 and output of the velocity vector calculation unit 16, and is designed to detect a stretch start timing when detection conditions are given by the detection condition registration unit 21.

Figure 5:
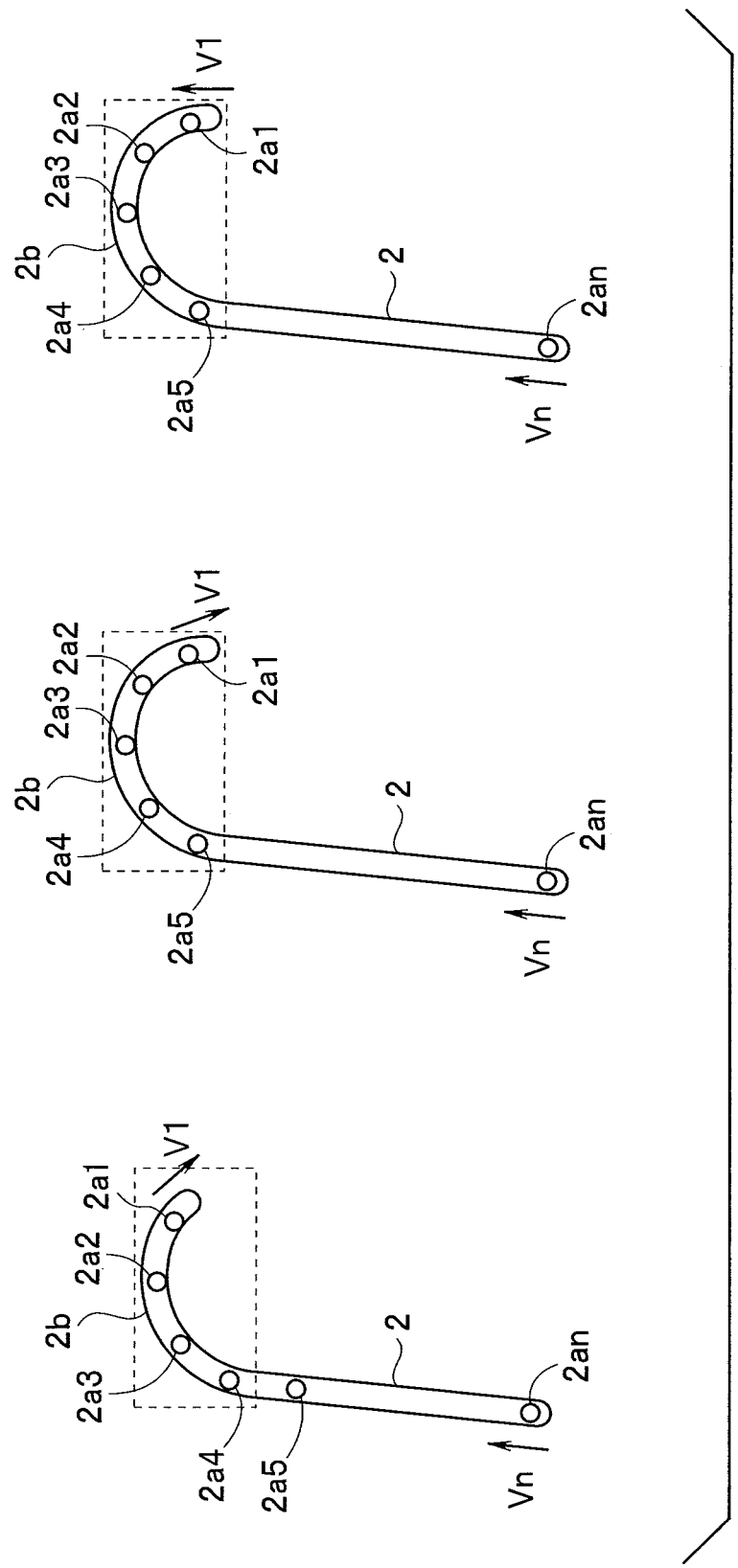
FIG. 5 is an explanatory diagram for illustrating a stretch start timing detection method used by a position determination unit 22.

FIG. 5 is an explanatory diagram for illustrating a stretch start timing detection method used by the position determination unit 22 and shows states just before and after a stretch start timing. FIG. 5 shows that transmitter coils 2*a*1, 2*a*2, . . . , 2*a*5 are placed starting from a distal end side of the bending portion 2*b* and that the transmitter coil 2*an* is placed within a predetermined distance from a proximal end side of the bending portion 2*b*. Velocity vectors of the transmitter coils 2*a*1 and 2*an* detected by the velocity vector calculation unit 16 are denoted by V1 and Vn, respectively.

The left part of FIG. 5 shows that the insertion portion 2 is inserted into the intestinal tract 1, the bending portion 2*b* reaches the stretchable part 1*a*, and the bending portion 2*b* gets into a bent state as indicated by a broken-line frame. The central part of FIG. 5 shows that the insertion portion 2 has been inserted further into the intestinal tract 1, and the inserted-state determination unit 18 detects the shape in the central part of FIG. 5 as a stick-like shape. In both the left part and central part of FIG. 5, both the velocity vectors V1 and Vn are oriented in the depth direction of the intestinal tract 1. In other words, when a proximal end side of the insertion portion 2 is pushed into the intestinal tract 1, the distal end of the insertion portion 2 moves in the depth direction in the intestinal tract 1.

On the other hand, the right part of FIG. 5 shows that the stretchable part 1*a* is stretching. In other words, in this case, the velocity vector V1 is oriented in such a direction as to stretch the intestinal tract 1, that is, in substantially the same direction as the velocity vector Vn, rather than in the depth direction of the intestinal tract 1. The position determination unit 22 determines the stretch start timing based on changes in the velocity vectors V1 and Vn.

In other words, after the direction of the velocity vector V1 changes 90 degrees or more with respect to the direction of the velocity vector Vn as in the left part and central part of FIG. 5, if the direction of the velocity vector V1 with respect to the direction of the velocity vector Vn becomes equal to or smaller than a predetermined angle (e.g., 30 degrees vs. a maximum possible value of 90 degrees) as in the right part of FIG. 5, the position determination unit 22 determines that the stretch start timing has been reached.

Note that whereas in the example of FIG. 1, the position determination unit 22 finds the stretch start timing based on changes in the velocity vectors V1 and Vn when the determination result produced by the inserted-state determination unit 18 indicates that the insertion portion 2 is shaped like a stick, the stretch start timing may be determined based only on changes in the velocity vectors V1 and Vn by omitting the determination of the insertion shape.

The position determination unit 22 is designed to set, in the stretch start timing, a position where the curvature of the bending portion 2*b* is the largest as a manual compression point that should be manually compressed. The position determination unit 22 finds the manual compression point that maximizes the curvature, using the position coordinates of the transmitter coils 2*a*.

For example, a curvature calculation unit 22*a* of the position determination unit 22 finds the curvature of the bending portion 2*b* at the position of the transmitter coil 2*a*2 from the position coordinates of the transmitter coils 2*a*1, 2*a*2, and 2*a*3, finds the curvature of the bending portion 2*b* at the position of the transmitter coil 2*a*3 from the position coordinates of the transmitter coils 2*a*2, 2*a*3, and 2*a*4, and finds the curvature of the bending portion 2*b* at the position of the transmitter coil 2*a*4 from the position coordinates of the transmitter coils 2*a*3, 2*a*4, and 2*a*5. The position determination unit 22 designates the position of the transmitter coil 2*a* that gives the largest of the curvatures of the three points found by the curvature calculation unit 22*a*, as the manual compression point.

Note that whereas in the example of FIG. 5, description has been given of a case in which curvatures at three locations are found from coordinates of five coil positions and a coil position that gives the largest curvature is found and designated as the manual compression point, curvatures may be found at two locations or four or more locations rather than three locations. Depending on size and the like of the bending portion 2*b*, it is also conceivable that the position that maximizes the curvature can be estimated in advance. In other words, by registering the position that is likely to maximize the curvature in the detection condition registration unit 21 with reference to the position of, for example, the transmitter coil 2*a*1 at the distal end of the insertion portion 2, the position that is likely to maximize the curvature may be found as the manual compression point from the position where the transmitter coil 2*a*1 is located in the stretch start timing.

Regardless of the curvature, the position determination unit 22 may also be designed to determine a position located at a predetermined length from a forefront of the insertion portion 2 or a position located at a predetermined length from a forefront of the bending portion 2*b* in the stretch start timing as the manual compression point.

The position determination unit 22 outputs coordinates of the found manual compression point to a shape generation unit 23. The shape generation unit 23 generates display data for compression position display around the coordinates of the manual compression point and outputs the display data to the display control unit 25.

Figure 6:
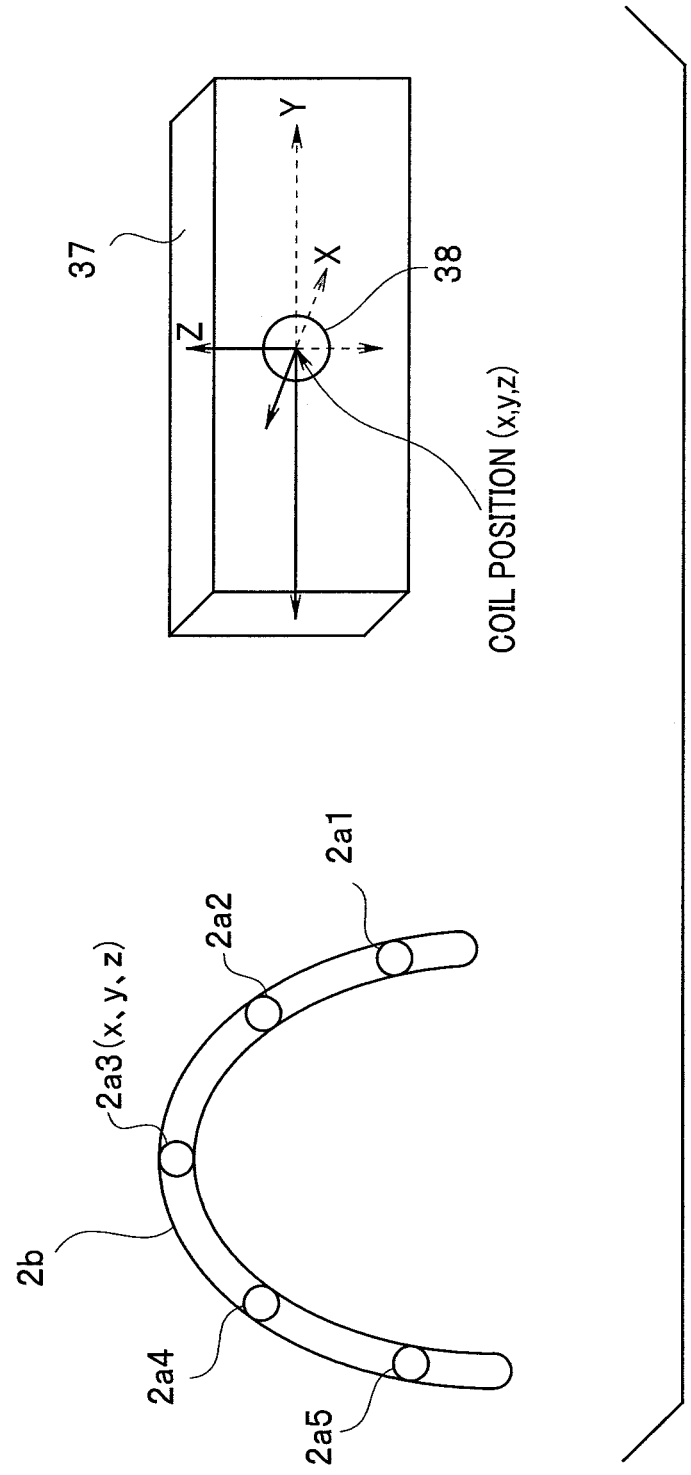
FIG. 6 is an explanatory diagram showing an example of compression position display.

FIG. 6 is an explanatory diagram showing an example of compression position display. The left part of FIG. 6 shows a state of the bending portion of the insertion portion 2. In the example of FIG. 5, of the transmitter coils 2*a*1 to 2*a*5 placed in the bending portion, the curvature is largest at the position of the transmitter coil 2*a*3. It is assumed that three-dimensional position coordinates of the transmitter coil 2*a*3 are (x, y, z). The right part of FIG. 6 explains display data for compression position display in this case, where the shape generation unit 23 generates display data for a compression position display 37 showing a cubic shape of a predetermined size around the position coordinates (x, y, z). Note that the shape generation unit 23 may generate display data for a compression position display 38 showing a spherical shape of a predetermined size around the position coordinates (x, y, z).

Using coordinate transformation, the display control unit 25 converts the display data for compression position display into information to be displayed on the monitor 35, where the display data has been received from the shape generation unit 23. Then, the display control unit 25 generates display data for use to simultaneously display an insertion shape image and the compression position display and outputs the display data to the monitor 35. This causes the insertion shape image and the compression position display to be displayed simultaneously on the display screen of the monitor 35.

Figure 7:
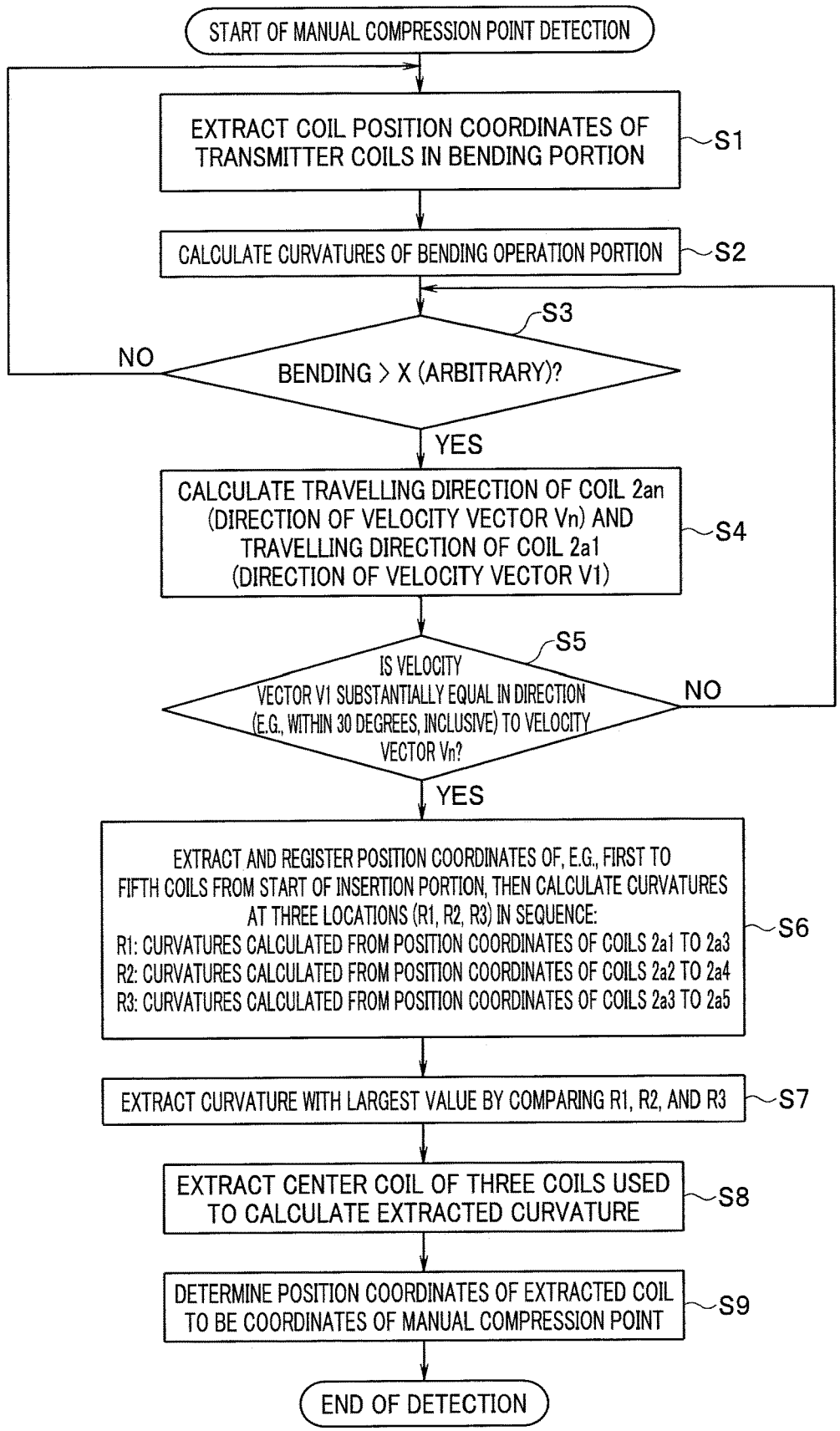
FIG. 7 is a flowchart for illustrating operation of the first embodiment.
Figure 8:
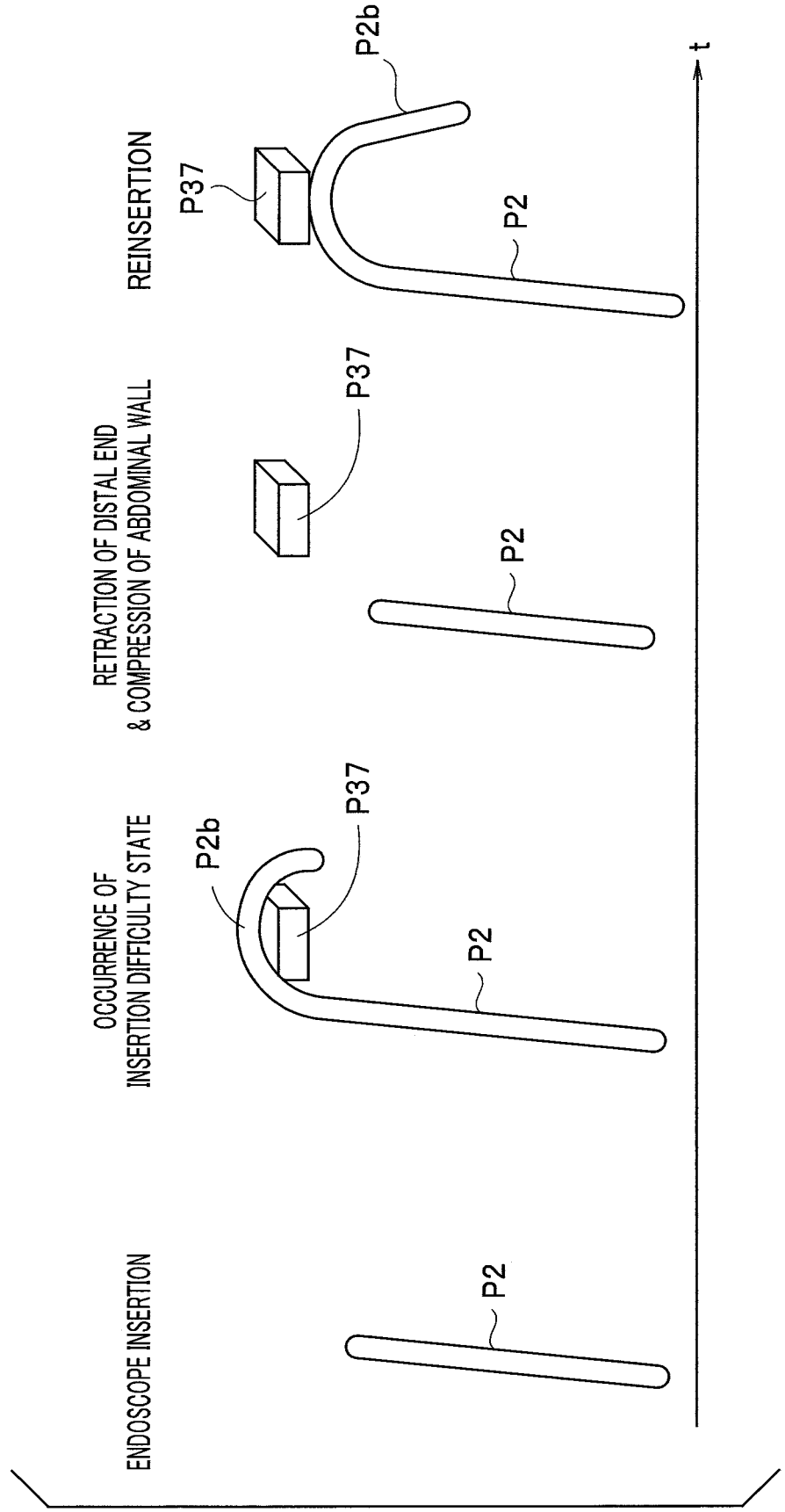
FIG. 8 is an explanatory diagram showing an example of display on a monitor 35 during insertion of an insertion portion 2.
Figure 9:
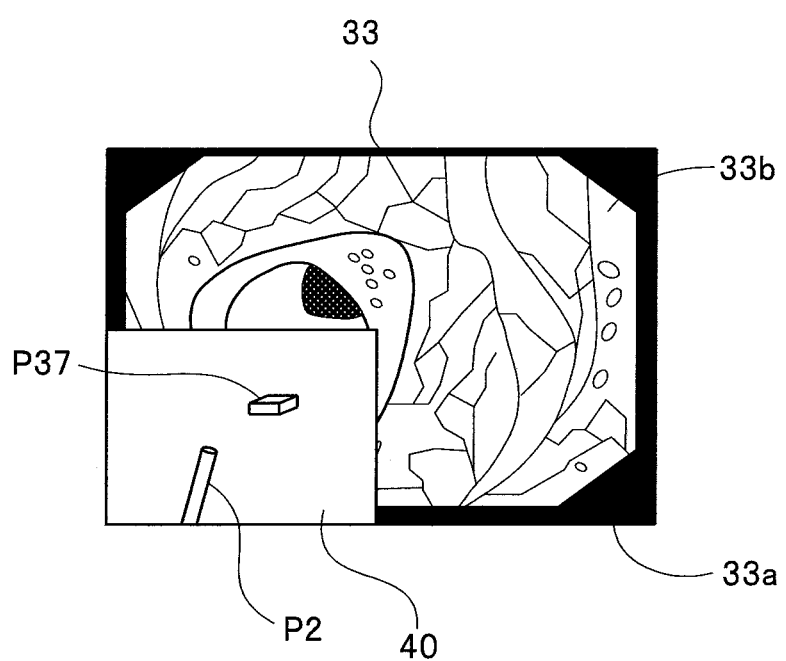
FIG. 9 is an explanatory diagram showing a display example on a monitor 33.

Next, operation of the embodiment configured in this way will be described with reference to FIGS. 7 to 9. FIG. 7 is a flowchart for illustrating operation of the first embodiment. FIG. 8 is an explanatory diagram showing an example of display on the monitor 35 during insertion of the insertion portion 2. FIG. 9 is an explanatory diagram showing a display example on the monitor 33.

Now, it is assumed as shown in FIG. 1 that the surgeon inserts through the anus the insertion portion 2 into the large intestine of the subject P lying on the examination bed 6. The endoscope insertion shape observation apparatus 10 finds three-dimensional position coordinates of the plurality of transmitter coils 2*a* incorporated in the insertion portion 2, at predetermined time intervals. In other words, by controlling the transmitter unit 19, the control unit 11 of the endoscope insertion shape observation apparatus 10 causes the transmitter unit 19 to supply high-frequency signals to the plurality of transmitter coils 2*a* with predetermined timings, respectively. The transmitter coils 2*a* supplied with the high-frequency signals generate electromagnetic waves accompanied by magnetic fields. The magnetic fields are received by respective coil blocks of the receiving antenna 7, and detection results corresponding to magnetic field strengths are captured into the position calculation unit 13 via the receiver unit 12 of the endoscope insertion shape observation apparatus 10.

The position calculation unit 13 has been provided by the control unit 11 with information about drive timings of respective transmitter coils 2*a* and finds three-dimensional position coordinates of each transmitter coil 2*a* from detection results of each transmitter coil 2*a* produced by coil blocks using a publicly known position estimation algorithm.

The position coordinates are supplied to the scope model generation unit 14, which then generates an insertion shape image based on the position coordinates. The plurality of transmitter coils 2*a* are placed at known positions at predetermined intervals along the shape of the insertion portion 2. In other words, the positions of the respective transmitter coils 2*a* are discrete positions in the insertion portion 2. By interpolating the discrete positions, the scope model generation unit 14 generates an insertion shape image corresponding to an approximate shape of the insertion portion 2. Note that the insertion shape image is found in a measurement coordinate system.

The scope model generation unit 14 gives the generated insertion shape image to the display control unit 25. The display control unit 25 displays the insertion shape image on the display screen of the monitor 35.

The output of the scope model generation unit 14 is also supplied to the shape detection unit 17. Based on the insertion shape image, the shape detection unit 17 detects a predetermined shape of the insertion portion 2 in the body cavity and outputs a detection result to the inserted-state determination unit 18. The inserted-state determination unit 18 determines whether the shape detected by the shape detection unit 17 is such a shape as to cause the intestinal tract 1 to stretch. In other words, if the shape detected by the shape detection unit 17 is, for example, a stick-like shape, the inserted-state determination unit 18 outputs a determination result to the detection condition registration unit 21, indicating that the insertion portion 2 is shaped to stretch the intestinal tract 1.

Note that the shape detection unit 17 and the inserted-state determination unit 18 may determine a shape that may cause the stretchable part 1a to stretch, based on a state of bending of the bending portion 2b on a distal end side of the insertion portion 2. Steps S1 to S3 in FIG. 7 show processes performed in this case, and in step S1, the shape detection unit 17 controlled by the control unit 11 extracts position coordinates (coil position coordinates) of the plurality transmitter coils 2a placed in the bending portion 2b. Next, in step S2, the shape detection unit 17 finds the curvatures at the respective coil positions, that is, the curvatures at various parts of the bending portion 2b using the coil position coordinates of the respective transmitter coils 2a, and outputs the curvatures to the inserted-state determination unit 18. The inserted-state determination unit 18 controlled by the control unit 11 may be designed to determine whether an average value of the curvatures of the various parts of the bending portion 2b is larger than a predetermined threshold X (step S3), and move to step S4 if the average value is larger than the threshold X, by determining that the shape is likely to be a stick-like shape. Note that if the determination in step S3 is "NO", the control unit 11 returns to step S1 and repeats steps S1 to S3.

A detection condition for sensing the stretch start timing has been registered in the detection condition registration unit 21, where the detection condition is, for example, that after the direction of the velocity vector V1 of the transmitter coil 2a1 changes 90 degrees or more with respect to the direction of the velocity vector Vn of the transmitter coil 2an, the direction of the velocity vector V1 with respect to the direction of the velocity vector Vn becomes equal to or smaller than a predetermined angle (e.g., 30 degrees). If the determination result produced by the inserted-state determination unit 18 indicates that the shape of the insertion portion 2 has become a predetermined shape that can cause the stretchable part 1a to stretch, the detection condition registration unit 21 controlled by the control unit 11 gives the registered detection condition to the position determination unit 22 and causes the position determination unit 22 to start sensing the stretch start timing.

The output of the position calculation unit 13 has also been given to the velocity vector calculation unit 16, which calculates the velocity vector Vn of the transmitter coil 2an and the velocity vector V1 of the transmitter coil 2a1 (step S4) and outputs calculation results to the position determination unit 22. In step S5, the position determination unit 22 controlled by the control unit 11 determines whether the velocity vector V1 is substantially equal in direction (within 30 degrees, inclusive) to the velocity vector Vn. Note that the angle used to determine the substantial equality can be set as appropriate up to a maximum of 90 degrees. If the determination in step S3 is "NO", the control unit 11 returns to step S3 and repeats steps S3 to S5.

At the time when a stick-like shape is detected in step S3, the direction of the velocity vector V1 is inclined 90 degrees or more with respect to the direction of the velocity vector Vn. However, in the stretch start timing, the velocity vector Vn oriented in the depth direction of the intestinal tract 1 changes direction and becomes substantially equal in direction to the velocity vector Vn. Thus, it is considered that a timing in which the determination in step S5 becomes "YES" is the stretch start timing.

If the determination in step S5 becomes "YES", the position determination unit 22 sets the position having a maximum curvature of the bending portion 2b in the stretch start timing as the manual compression point. In other words, in step S6, the curvature calculation unit 22a of the position determination unit 22 calculates the curvatures of the bending portion 2b at the positions of the respective transmitter coils 2a using the output of the position calculation unit 13.

In FIG. 7, step S6 shows an example in which the curvature calculation unit 22a of the position determination unit 22 finds three curvatures R1 to R3 in placement locations of the transmitter coils 2a2 to 2a4 using the first to fifth transmitter coils 2a1 to 2a5 from a start position of the insertion portion 2. The position determination unit 22 extracts the largest of the calculated curvatures R1 to R3 (step S7) and selects the center coil of the three coils used to calculate the extracted curvature (step S8). The position determination unit 22 determines the position coordinates of the coil selected in step S8, to be the coordinates of the manual compression point (step S9). In other words, in steps S6 to S9 of FIG. 7, of the coil positions of the plurality of coils 2a placed in the bending portion 2b, the coil position with the largest curvature is set as the manual compression point.

The position determination unit 22 gives the determined position coordinates of the manual compression point to the shape generation unit 23, which then generates display data of a compression position display including the position coordinates. The display data is given to the display control unit 25 and converted into display data to be displayed on the monitor 35. In this way, the display control unit 25 causes the insertion shape image from the scope model generation unit 14 and the compression position display to be displayed simultaneously on the display screen of the monitor 35.

FIG. 8 shows display examples presented on the monitor 35 during a series of insertion procedures. FIG. 8, in which the horizontal axis represents time, shows changes in display presented on the monitor 35 as a series of procedures proceeds. Just after the insertion portion 2 starts being inserted (endoscope insertion), the insertion portion moves ahead linearly and a linear insertion shape image P2 is displayed on the monitor 35. When the insertion portion 2 reaches the stretchable part 1a and the bending portion 2b bends, making the stretchable part 1a stretch and thereby making insertion difficult, the position determination unit 22 detects a stretch start timing, finds a manual compression point from the bent state of the bending portion 2b, and causes a compression position display P37 to be presented on the monitor 35, indicating the manual compression point. Note that in FIG. 8, the surgeon causes the insertion portion 2 to move ahead further even after the stretch start timing, with the result that the intestinal tract 1 stretches and an image part P2b of the bending portion 2b is located above the display position of the compression position display P37.

When recognizing that stretching has occurred based on sensation in the hand inserting the insertion portion 2, display on the monitor 35, or the like, the surgeon retracts the insertion portion 2 once. Consequently, as shown in FIG. 8, the insertion shape image P2 returns to the original linear shape. According to the present embodiment, regardless of the inserted state of the insertion portion 2, the compression position display P37 continues to be presented. By referring to the compression position display P37, the caregiver can easily grasp the position to be manually compressed.

By referring to the compression position display P37 and the display of the insertion shape image P2, the caregiver performs manual compression. When the insertion portion 2 is inserted in this state, the insertion portion 2 moves ahead relatively easily in the depth direction of the intestinal tract 1 even in the stretchable part 1a. The reinsertion in FIG. 8 shows this state, where the image part P2b of the bending portion 2b moves ahead in the depth direction of the intestinal tract 1 by passing near the manual compression point shown in the compression position display P37.

Note that the display in FIG. 8 can also be presented on the monitor 33 for use to display the endoscopic image 33b. The display control unit 25 outputs display data to the control unit 11. The control unit 11 gives the display data from the display control unit 25 to the video processor/light source 31 via the transmitter unit 19. Consequently, as shown in FIG. 9, the video processor/light source 31 causes the endoscopic image 33b acquired by the endoscope 32 to be displayed simultaneously with an insertion assistance image 40 including the insertion shape image P2 and the compression position display P37 on the display screen 33a of the monitor 33.

In this way, the present embodiment detects the stretch start timing of the intestinal tract, finds a manual compression point from the bent state of the bending portion in the stretch start timing, and causes the compression position display that indicates the position of the manual compression point to be displayed together with an insertion shape image. By setting a target for a compression position with reference to the display, the caregiver can smoothly perform manual compression.

Modification

Figure 10:
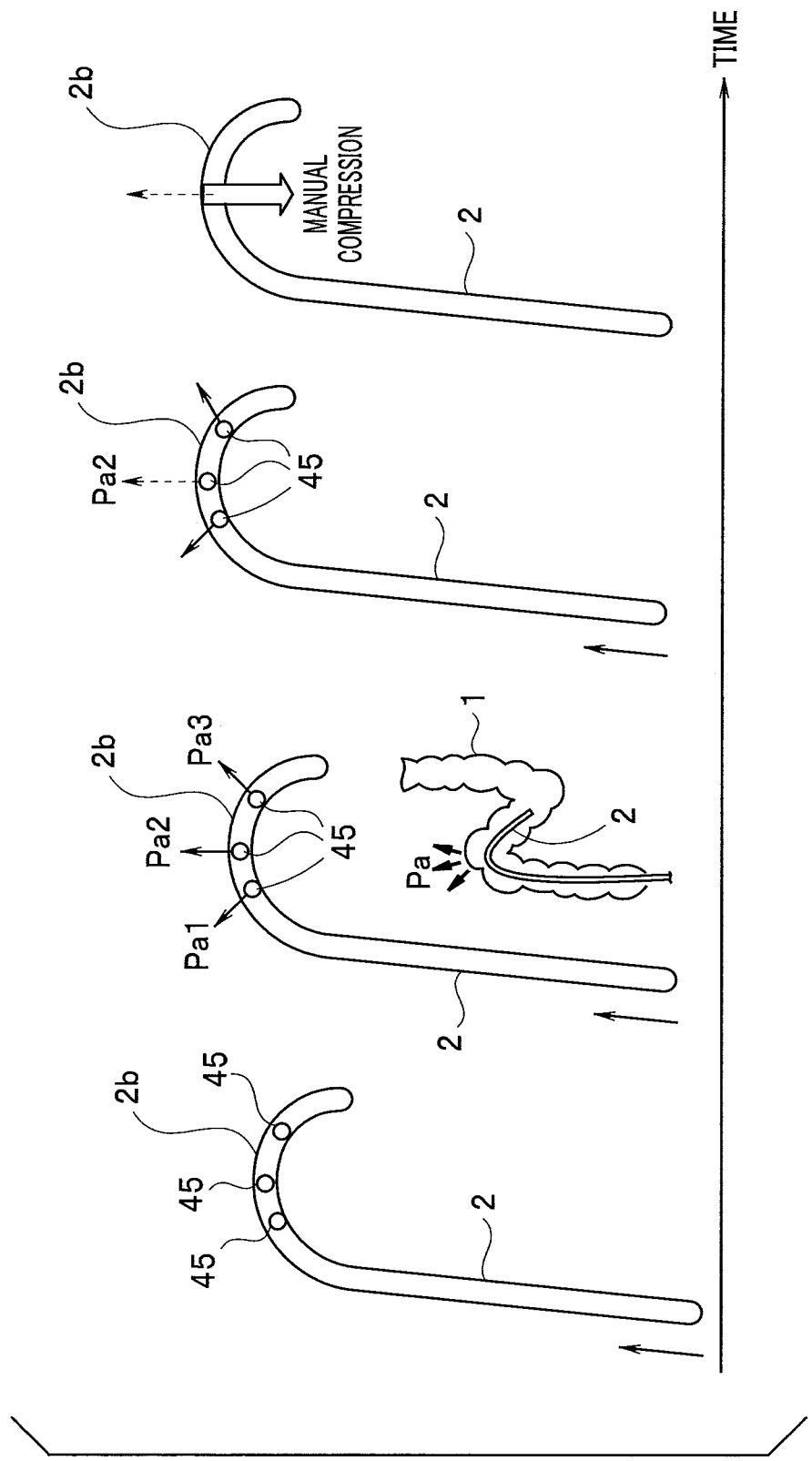
FIG. 10 is an explanatory diagram showing a modification.

FIG. 10 is an explanatory diagram showing a modification. Whereas in the above embodiment, description has been given of an example in which the manual compression point is found using velocity vectors and curvatures, according to the present modification, the manual compression point is found using pressure sensors. As shown in FIG. 10, a plurality of pressure sensors 45 are disposed in the bending portion 2b of the insertion portion 2. The pressure sensors 45 sense pressing forces against inner walls of the intestinal tract 1. FIG. 10, in which the horizontal axis represents time, shows changes in pressing force sensed by the pressure sensors 45 as procedures proceed. The first part of FIG. 10 from the left shows that the insertion portion 2 moves ahead smoothly in the intestinal tract 1. The second part of FIG. 10 shows that the intestinal tract 1 is stretched by entry of the insertion portion 2 and pressing forces Pa are generated by the insertion portion 2. In the example of FIG. 10, pressing forces Pa1 to Pa3 are sensed by the respective sensors 45.

The third part of FIG. 10 shows that, of sensing outputs of the three sensors 45, the pressing force Pa2 sensed by the center sensor is the largest. According to the present modification, a stretch start timing is determined when sensor outputs of the respective sensors 45 become higher than a predetermined threshold and a sensor position at which the largest pressing force is sensed in the stretch start timing is set as the manual compression point. The right part of FIG. 10 shows that when manual compression is performed at the manual compression point set in this way, stretching of the intestinal tract 1 is suppressed against the pressing force Pa2 and the insertion portion 2 can move ahead smoothly.

In this way, the present modification provides advantages similar to the advantages of the first embodiment.

Second Embodiment

Figure 11:
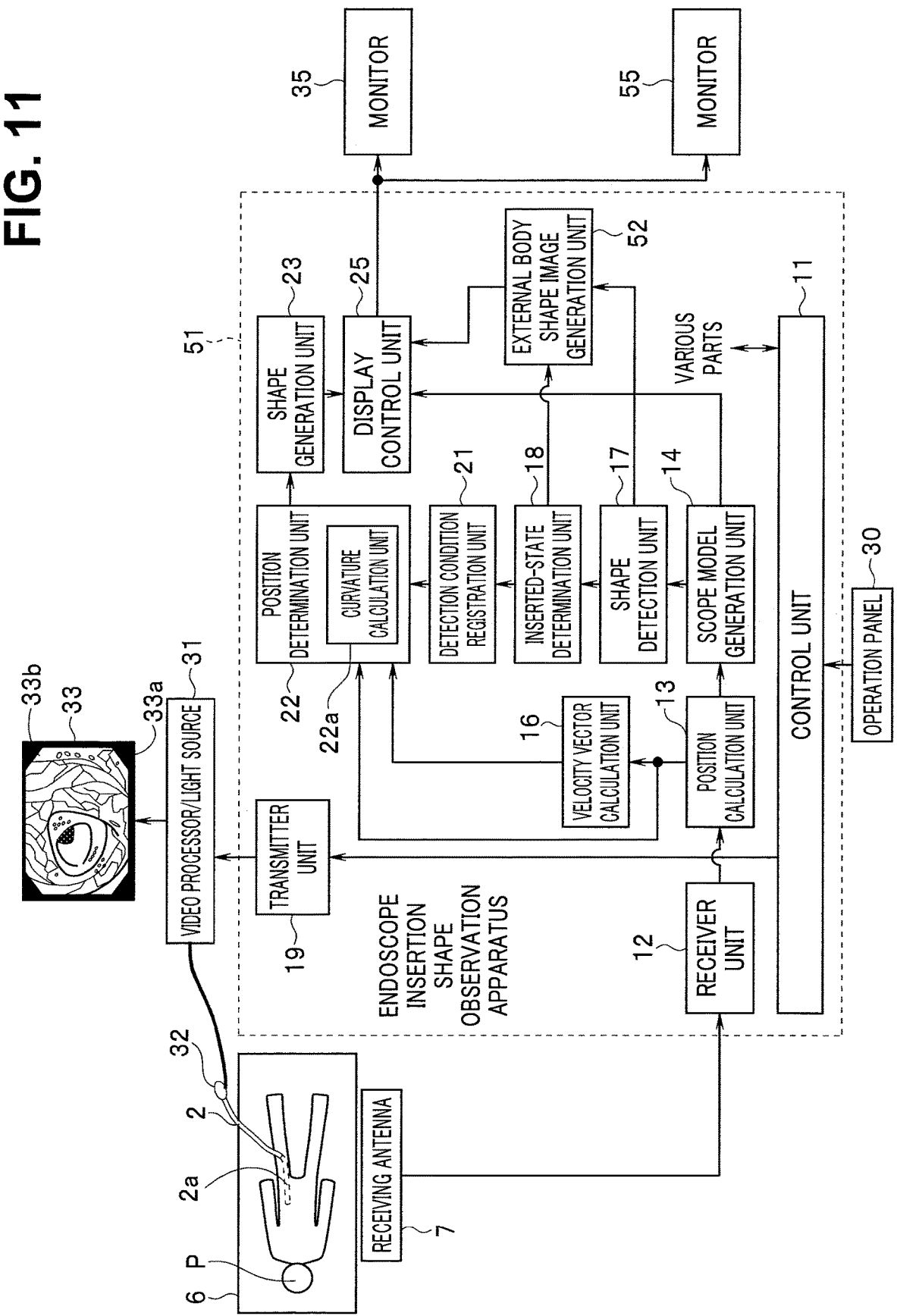
FIG. 11 is a block diagram showing a second embodiment of the present invention.

FIG. 11 is a block diagram showing a second embodiment of the present invention. In FIG. 11, the same components as the components in FIG. 1 are denoted by the same reference numerals as the corresponding components in FIG. 1, and description of the same components will be omitted. In the first embodiment, description has been given of an example in which an insertion shape image and a compression position display are caused to be presented on the monitor. The present embodiment causes an external body shape image to be displayed as well.

An endoscope insertion shape observation apparatus 51 according to the present embodiment is provided with an external body shape image generation unit 52 configured to output display data of an external body shape image. The external body shape image refers to a human body diagram, an anatomical chart, and the like that can show a build such as a body shape itself or physique of a patient. The external body shape image may be a schematic image just enough to allow the build to be seen or a detailed image including an image part of an organ such as a large intestinal tract model. The external body shape image does not need to be limited to 2D images, and a technique that can use stereoscopy such as 3D images may be adopted.

The external body shape image generation unit 52 is designed to hold display data of an external body shape image in a non-illustrated memory and output the display data of the external body shape image to the display control unit 25 under the control of the control unit 11. The display control unit 25 outputs the external body shape image received from the external body shape image generation unit 52 to the monitor 35 by converting the image into such a format as to be displayed on the monitor 35.

Note that the external body shape image generation unit 52 may be designed to hold the display data of a plurality of the external body shape images in the memory and output the display data of one external body shape image selected under the control of the control unit 11 to the display control unit 25.

For example, the external body shape image generation unit 52 may hold the display data of the plurality of external body shape images ranging in size from the smallest size of S to the largest size of XXL in the memory and the control unit 11 may be designed to select the display data of an external body shape image of a size corresponding to the value of BMI/height of the patient and output the display data to the display control unit 25.

Furthermore, the external body shape image generation unit 52 may be configured to generate the external body shape image based on the height and waist size of the patient. The external body shape image generation unit 52 may also be configured to generate the external body shape image including the navel and diaphragm of a human body based on anatomical information.

To display the external body shape image and the insertion shape image in a state of being aligned with each other, the present embodiment is designed to display the external body shape image simultaneously with the insertion shape image and the compression position display by bringing a predetermined position of the external body shape image (hereinafter referred to as an external body shape image reference position) corresponding to a predetermined position of the subject (hereinafter referred to as a subject reference position) into coincidence with a predetermined position of the insertion shape image (hereinafter referred to as an insertion shape image reference position) corresponding to the subject reference position. For example, the position of the anus of the subject P is set as the subject reference position based on the spatial position coordinates calculated by the position calculation unit 13.

For example, with the distal end (position of the transmitter coil 2*a*1) of the insertion portion 2 placed near the anus of the subject P, the surgeon operates the operation panel 30 to specify the subject reference position for the control unit 11. Consequently, the control unit 11 causes the transmitter unit 19 to apply a high-frequency sinusoidal wave to the transmitter coil 2*a*1 and causes the position calculation unit 13 to acquire the coil position at the distal end of the insertion portion 2 in the measurement coordinate system, that is, anus position coordinates. In this way, the control unit 11 can obtain position coordinates of anus position from the output of the position calculation unit 13 with an operation timing of the operation panel 30. The control unit 11 is designed to hold the position coordinates of the anus position of the subject P and output the position coordinates to the display control unit 25.

By bringing the external body shape image reference position into coincidence with a predetermined position (hereinafter referred to as a display reference position) on the display screen of the monitor 35, the display control unit 25 displays the external body shape image on the display screen. For example, the display control unit 25 sets the display reference position to a lowermost end portion at a center in a left-right direction of the display screen and displays the external body shape image such that the anus position (external body shape image reference position) on the external body shape image is located at the display reference position. The display control unit 25 causes the insertion shape image to be displayed such that an image part corresponding to the anus position on the insertion shape image is located at the display reference position, that is, the lowermost end portion at the center in the left-right direction of the display screen.

Figure 12:
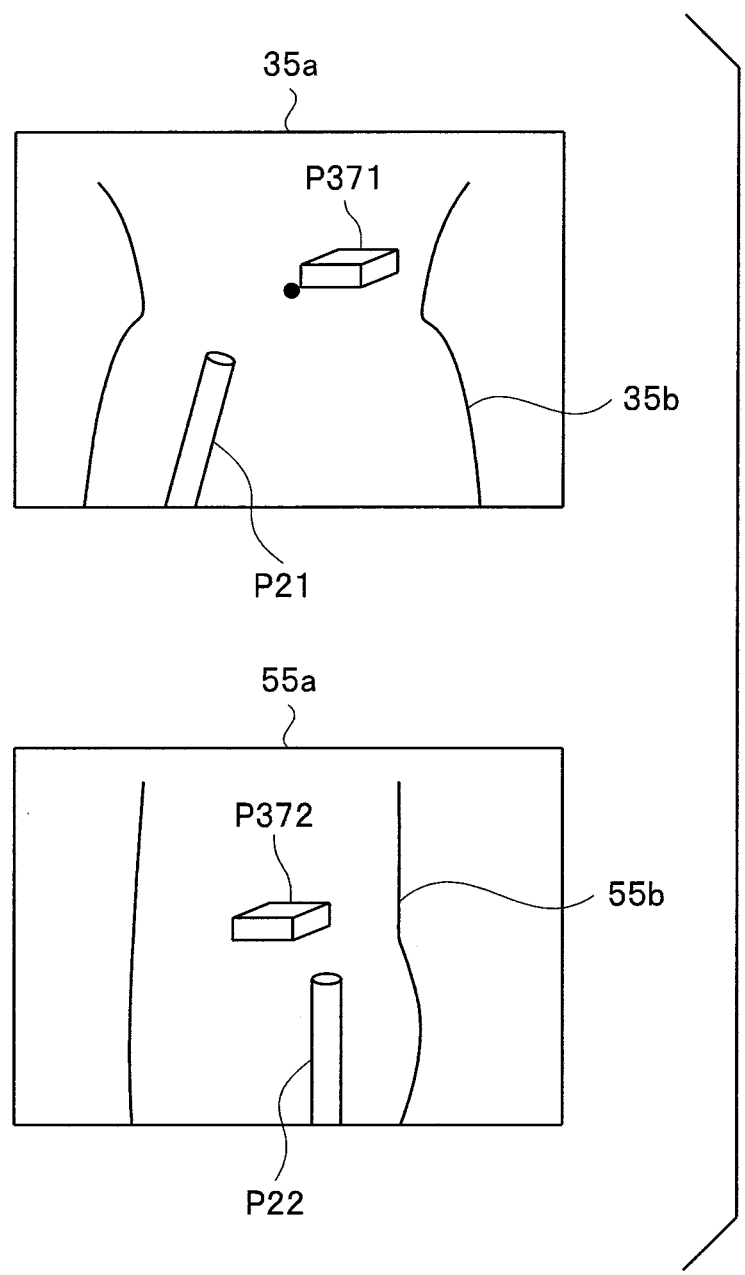
FIG. 12 is an explanatory diagram showing display examples in the second embodiment.

FIG. 12 is an explanatory diagram showing display examples in the second embodiment.

By changing transformation method of display coordinate transformation, the display control unit 25 is capable of displaying images observed from different angles on the monitor 35 and a monitor 55.

As shown in FIG. 12, the display control unit 25 displays an external body shape image 35*b* received from the external body shape image generation unit 52 as well as an insertion shape image P21 received from the scope model generation unit 14 and a compression position display P371 received from the shape generation unit 23 on a display screen 35*a* of the monitor 35. Note that the external body shape image 35*b* shows the subject P observed from the front.

The display control unit 25 also displays an external body shape image 55*b* received from the external body shape image generation unit 52 as well as an insertion shape image P22 received from the scope model generation unit 14 and a compression position display P372 received from the shape generation unit 23 on a display screen 55*a* of the monitor 55. Note that the external body shape image 55*b* shows the subject P observed from the left side.

In this way, in addition to providing advantages similar to the advantages of the first embodiment, the present embodiment can make the external body shape image displayed in superposition with the insertion shape image and the compression position display, allowing the caregiver to more easily grasp the manual compression position, using the compression position display.

Third Embodiment

Figure 13:
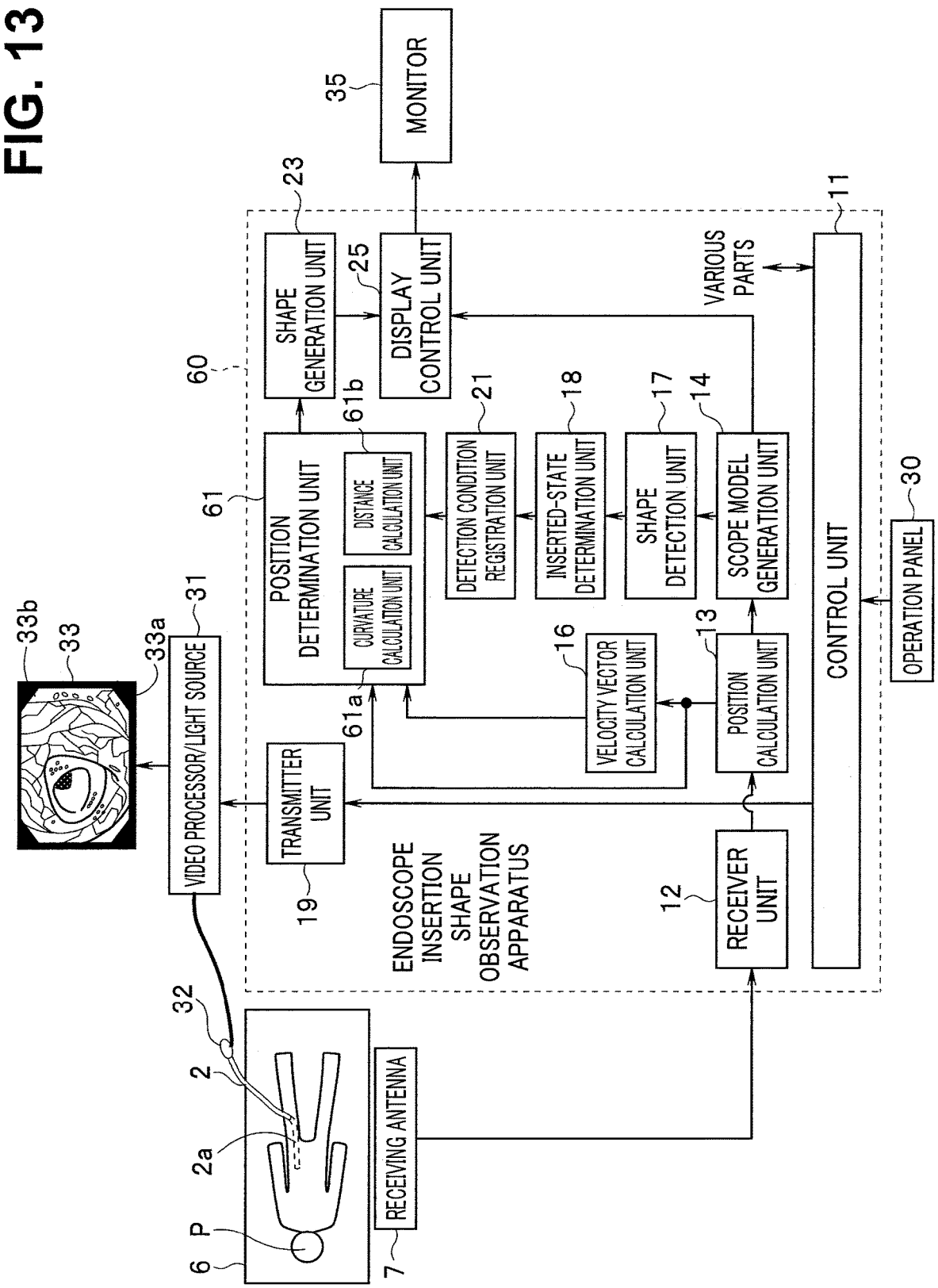
FIG. 13 is a block diagram showing a third embodiment of the present invention.

FIG. 13 is a block diagram showing a third embodiment of the present invention. In FIG. 13, the same components as the components in FIG. 1 are denoted by the same reference numerals as the corresponding components in FIG. 1, and description of the same components will be omitted. According to the present embodiment, the compression position display is presented only when needed and turned off when no longer needed.

An endoscope insertion shape observation apparatus 60 according to the present embodiment differs from the first embodiment in that a position determination unit 61 is adopted instead of the position determination unit 22. The position determination unit 61 is provided with a curvature calculation unit 61*a* and is capable of operation similar to the operation of the position determination unit 22, In other words, the position determination unit 61 is designed to be able to detect a stretch start timing, calculate the curvatures of the bending portion 2*b* at the positions of the respective coils 2*a* using the curvature calculation unit 61*a* and set a position with the largest curvature as a manual compression point.

The position determination unit 61 includes a distance calculation unit 61*b*. The distance calculation unit 61*b* is designed to detect after compression position display that the distal end of the insertion portion 2 has moved ahead in the depth direction of the intestinal tract 1 further than in the compression position display, based on the velocity vectors found by the velocity vector calculation unit 16 and the output of the position calculation unit 13, and turn off (hide) the compression position display when the distal end of the insertion portion 2 is spaced away from the manual compression point by a predetermined distance. For example, the position determination unit 61 may stop presenting the compression position display by giving a display-off control signal to the display control unit 25 via the shape generation unit 23.

Figure 14:
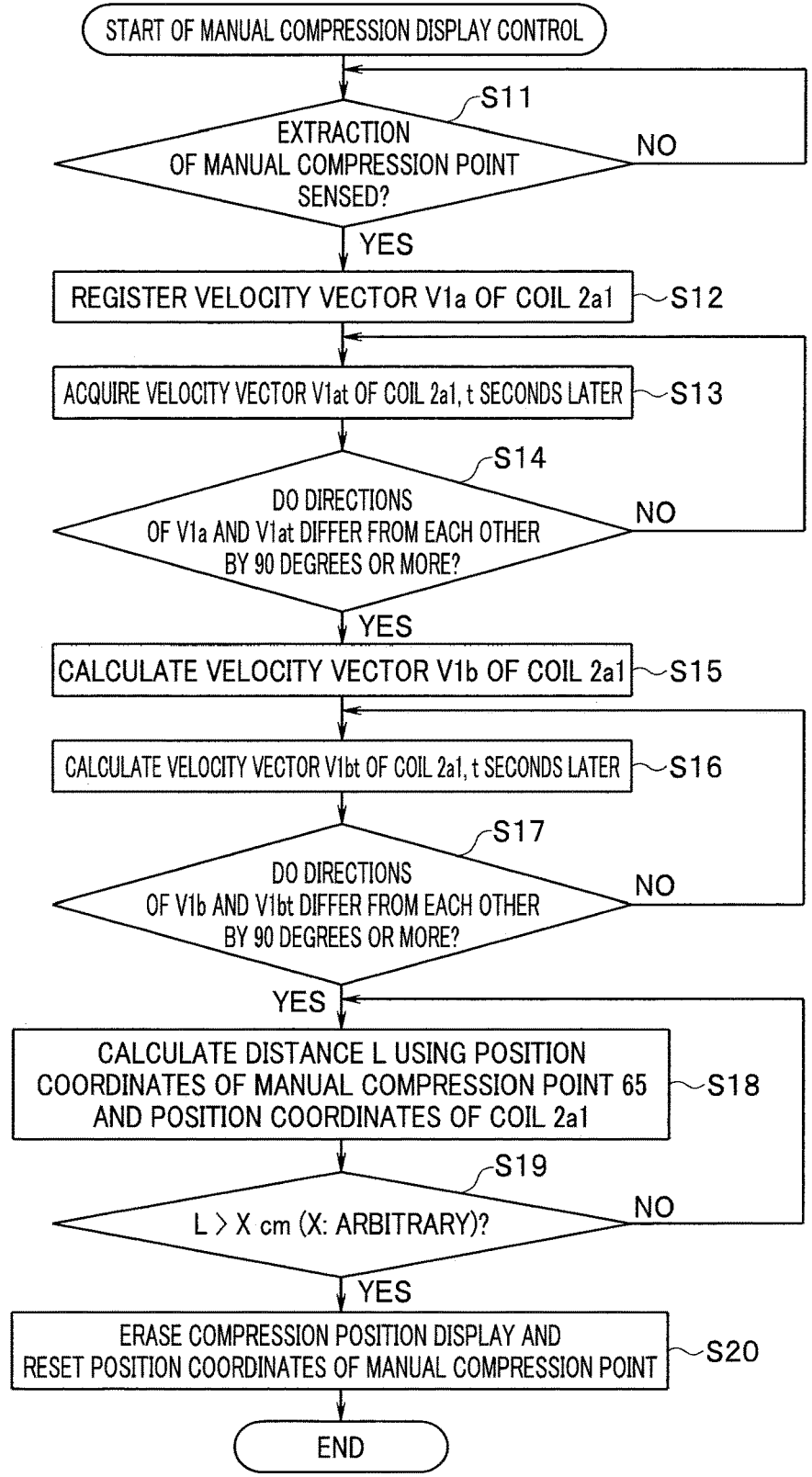
FIG. 14 is a flowchart for illustrating operation of the third embodiment.
Figure 15:
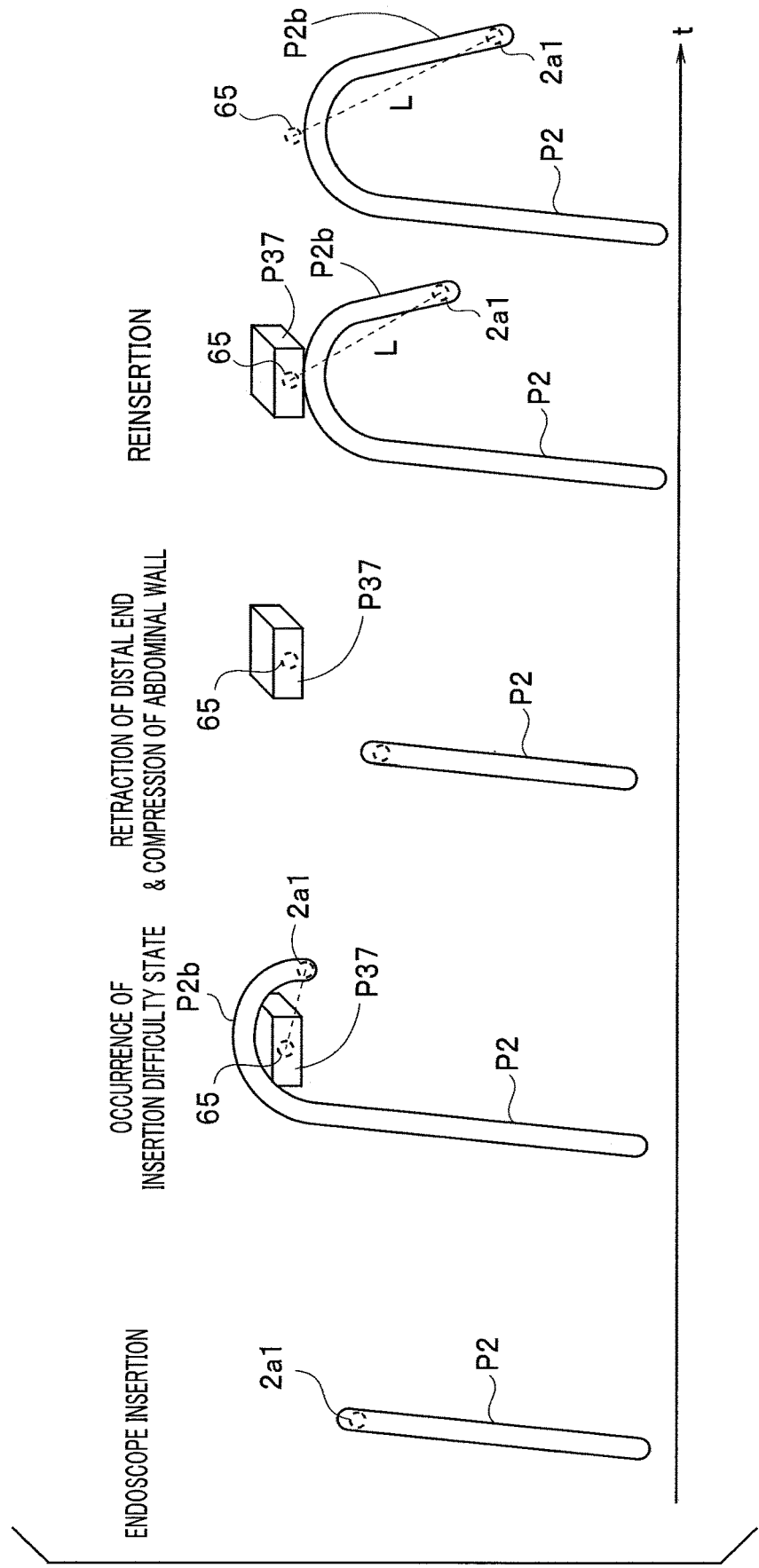
FIG. 15 is an explanatory diagram showing an example of display on the monitor 35 during insertion of the insertion portion 2.

Next, operation of the embodiment configured in this way will be described with reference to FIGS. 14 and 15. FIG. 14 is a flowchart for illustrating operation of the third embodiment. FIG. 15 is an explanatory diagram showing an example of display on the monitor 35 during insertion of the insertion portion 2.

According to the present embodiment, the surgeon starts inserting the insertion portion 2 through the anus into the large intestine of the subject P lying on the examination bed 6, and the insertion shape image and the compression position display are presented on the display screen of the monitor 35, and the operation of the present embodiment is similar to the first embodiment up to when reinsertion is performed.

FIG. 15 shows how things go in this case. FIG. 15, in which the horizontal axis represents time as with FIG. 8, shows changes in display presented on the monitor 35 as a series of procedures proceeds. The first to fourth display examples in FIG. 15 from the left are similar to the display examples in FIG. 8, where the insertion portion 2 is reinserted smoothly by manual compression.

According to the present embodiment, as shown in the fifth display example of FIG. 15 from the left, when a distance L between a manual compression point 65 and the transmitter coil 2a1 exceeds a predetermined threshold, the compression position display is determined to be unnecessary and is erased. However, since the distal end is retracted and reinserted, a determination as to whether to turn off the compression position display cannot be made based simply on the distance L. Thus, the present embodiment is designed to detect in step S11 whether the manual compression point 65 has been extracted.

If insertion difficulty state occurs in FIG. 15 and the manual compression point 65 is detected, the position determination unit 61 controlled by the control unit 11 outputs position coordinates of the manual compression point 65 to the shape generation unit 23 as with the first embodiment, then moves from step S11 to step S12, and acquires from the velocity vector calculation unit 16 a velocity vector V1$a$ of the transmitter coil 2a1 occurring in a stretch start timing, and registers the velocity vector V1$a$. In step S13 next, the position determination unit 61 acquires a velocity vector V1$at$ of the transmitter coil 2a1 occurring t seconds later. In step S14 next, the position determination unit 61 compares directions between the velocity vector V1$a$ and the velocity vector V1$at$ and determines whether the directions differ from each other by 90 degrees or more. If the direction of the velocity vector V1$at$ is inclined less than 90 degrees with respect to the direction of the velocity vector V1$a$, the position determination unit 61 returns to step S13, acquires the velocity vector V1$at$ of the transmitter coil 2a1, t more seconds later, and makes the comparison of step S14.

When the manual compression point 65 is detected, the direction of the velocity vector V1$a$ is substantially opposite the depth direction of the intestinal tract 1 and is inclined at least 90 degrees or more with respect to the depth direction. When the manual compression point 65 is detected, the insertion portion 2 is shaped like a stick as shown in FIG. 15, and when the distal end is retracted in FIG. 15, after a lapse of a predetermined time, the velocity vector V1$at$ of the transmitter coil 2a1 becomes oriented in a direction substantially opposite the direction of the velocity vector V1$a$, differing by at least 90 degrees or more. In other words, a "YES" determination in step S14 indicates that the distal end has been retracted.

If retraction of the distal end is detected in step S14, in steps S15 to S17, the position determination unit 61 performs processes similar to steps S12 to S14. In other words, in step S15, the position determination unit 61 acquires a velocity vector V1$b$ of the transmitter coil 2a1 from the velocity vector calculation unit 16 and registers the velocity vector V1$b$. In step S16 next, the position determination unit 61 acquires a velocity vector V1$bt$ of the transmitter coil 2a1 occurring t seconds later. In step S17, the position determination unit 61 compares directions between the velocity vector V1$b$ and the velocity vector V1$bt$ and determines whether the directions differ from each other by 90 degrees or more. If the direction of the velocity vector V1$bt$ is inclined less than 90 degrees with respect to the direction of the velocity vector V1$b$, the position determination unit 61 returns to step S16, acquires the velocity vector V1$bt$ of the transmitter coil 2a1, t more seconds later, and makes the comparison of step S17.

In other words, the comparison of step S17 is intended to determine whether the distal end of the insertion portion 2 is moving ahead in the depth direction of the intestinal tract 1 after passing near the manual compression point 65 as a result of reinsertion after retraction. If the determination in step S17 becomes "YES", the position determination unit 61 determines that the distal end of the insertion portion 2 is inserted smoothly as a result of the reinsertion. In step S18, the position determination unit 61 calculates the distance L between the manual compression point 65 and the transmitter coil 2a1 using the position coordinates of the manual compression point 65 and the position coordinates of the transmitter coil 2a1. In step S19, the position determination unit 61 determines whether the distance L has exceeded a predetermined threshold X cm.

The position determination unit 61 repeats the calculation of the distance L in step S18 until the distance L exceeds the predetermined threshold X cm. When the distance L exceeds the predetermined threshold X cm, the position determination unit 61 moves to step S19 and erases the compression position display P37. For example, the position determination unit 61 instructs the display control unit 25, via the shape generation unit 23, to stop presenting the compression position display. The position determination unit 61 also resets the position coordinates of the manual compression point. In this way, as shown in the fifth display example of FIG. 15 from the left, the compression position display P37 no longer needed is turned off.

In this way, in addition to providing advantages similar to the advantages of the first embodiment, the present embodiment provides the advantage of being able to erase the compression position display that is no longer needed.

Fourth Embodiment

Figure 16:
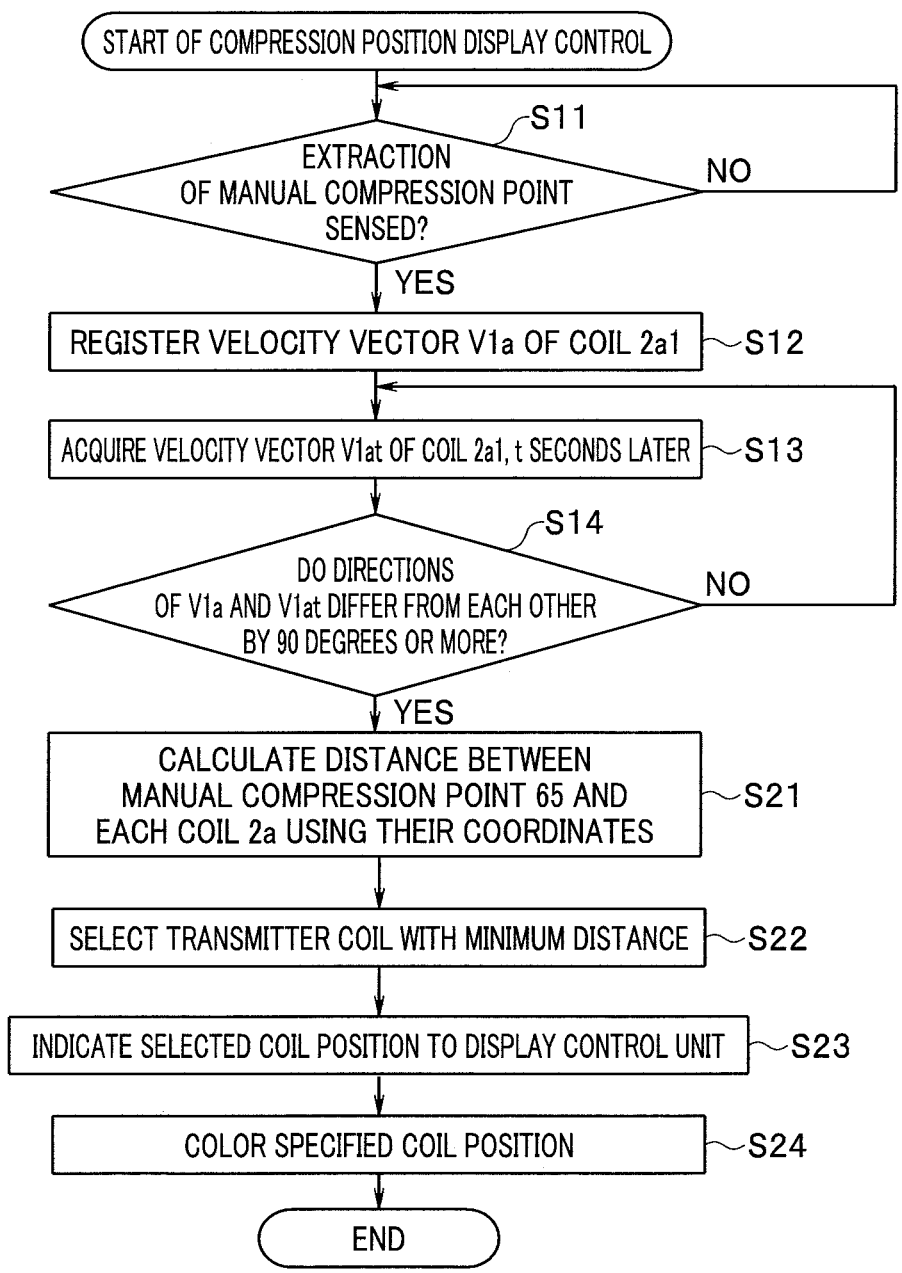
FIG. 16 is a flowchart showing a fourth embodiment of the present invention.

FIG. 16 is a flowchart showing a fourth embodiment of the present invention. In FIG. 16, the same procedures as the components in FIG. 14 are denoted by the same reference numerals as the corresponding procedures in FIG. 14, and description of the same procedures will be omitted. A hardware configuration of the present embodiment is similar to the hardware configuration in FIG. 13. The present embodiment is an example of displaying a coil position adjacent to a manual compression point in color.

The present embodiment is designed such that during reinsertion, the part of the insertion shape image which corresponds to a coil position adjacent to a manual compression point is colored in a color different from other part by the position determination unit 61 and the display control unit 25.

Figure 17:
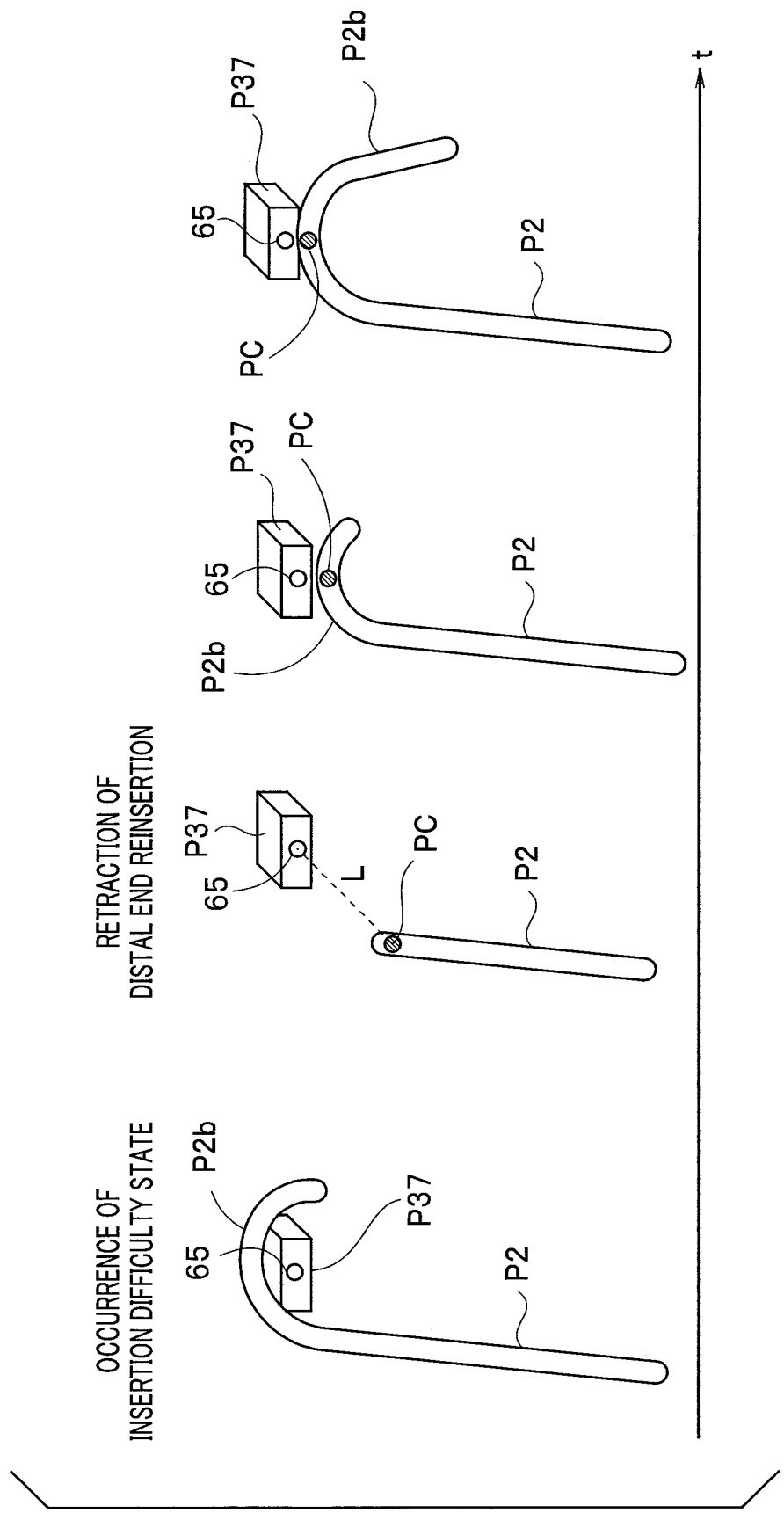
FIG. 17 is an explanatory diagram showing an example of display on the monitor 35 during insertion of the insertion portion 2 in the fourth embodiment, where the display is presented by a display method similar to the display method in FIG. 15.

FIG. 17 is an explanatory diagram showing an example of display on the monitor 35 during insertion of the insertion portion 2, where the display is presented by a display method similar to the display method in FIG. 15. The first display example of FIG. 17 from the left is similar to the second display example "insertion difficulty state" of FIG. 15 from the left and the second display example of FIG. 17 from the left shows that the "insertion difficulty state" has caused the insertion portion 2 to be retracted.

In FIG. 16, as with FIG. 14, steps S11 to S14 determine whether the insertion portion 2 has been retracted. If it is detected in step S14 that the insertion portion 2 has been retracted, the position determination unit 61 moves to step S21 and calculates a distance between the manual compression point 65 and each transmitter coil 2a using the distance calculation unit 61b. In step S22 next, the position determination unit 61 selects the transmitter coil with a minimum distance to the manual compression point 65 and outputs information about the selected coil position to the display control unit 25 via the shape generation unit 23.

Under the control of the control unit 11, the display control unit 25 applies predetermined coloring to the part on the insertion shape image which corresponds to the specified coil position (step S24). A colored display PC, that is, a diagonally shaded area, in FIG. 17 indicates the position of the transmitter coil determined to be closest to the manual compression point 65. At the start of reinsertion after retraction of the insertion portion 2, as shown in the second display example of FIG. 17 from the left, the colored display PC is provided in the position of the transmitter coil 2a1 at the distal end of the insertion portion 2.

The third display example of FIG. 17 from the left shows how the bending portion 2b of the insertion portion 2 passes near the manual compression point 65 as a result of manual compression. The fourth display example of FIG. 17 from the left shows that reinsertion of the insertion portion 2 is performed smoothly and that the colored display PC is provided at a coil position closer to the proximal end side than the bending portion 2b.

In this way, in addition to providing advantages similar to the advantages of the first embodiment, the present embodiment makes it possible to verify by means of colored display that insertion is performed smoothly after reinsertion.

Fifth Embodiment

Figure 18:
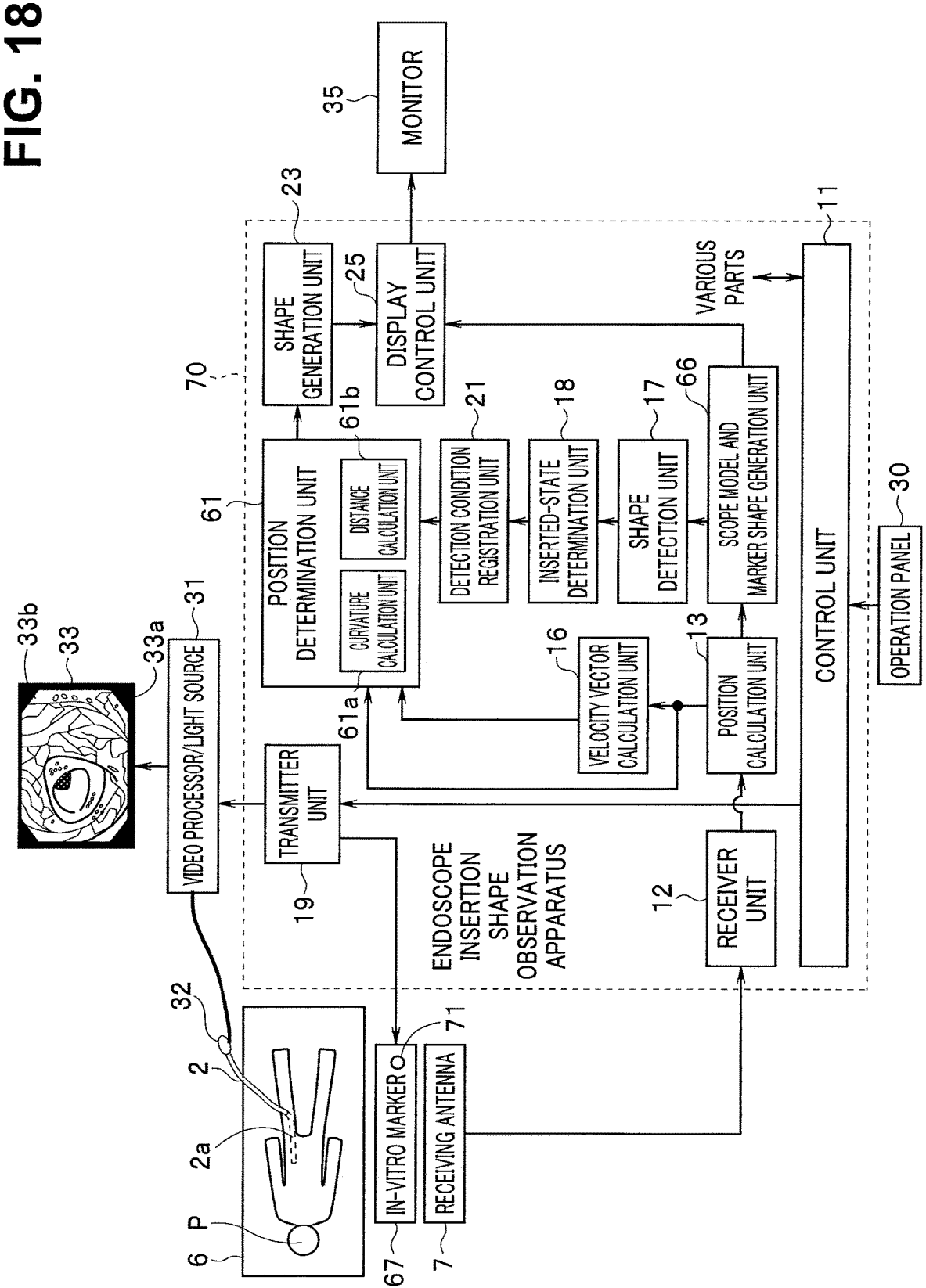
FIG. 18 is a block diagram showing a fifth embodiment of the present invention.

FIG. 18 is a block diagram showing a fifth embodiment of the present invention. In FIG. 18, the same components as the components in FIG. 13 are denoted by the same reference numerals as the corresponding components in FIG. 13, and description of the same components will be omitted. The present embodiment not only presents an insertion shape image and a compression position display that indicates the manual compression point, but also displays an actual manual compression position for the caregiver in order to further assist the caregiver in carrying out manual compression procedures.

The present embodiment differs from the embodiment shown in FIG. 13 in that an in-vitro marker 67 is added and that the present embodiment uses an endoscope insertion shape observation apparatus 70 that adopts a scope model and marker shape generation unit 66 instead of the scope model generation unit 14.

The in-vitro marker 67 is shaped and sized to be, for example, grippable by the caregiver and the like and configured to be movable outside the body of a patient P in response to hand movements of the caregiver and the like. The in-vitro marker 67 incorporates a transmitter coil 71, which is designed to be driven by a high-frequency signal supplied from the control unit 11 via the transmitter unit 19. When supplied with the high-frequency signal, the transmitter coil 71 generates an electromagnetic wave accompanied by a magnetic field. It is designed such that the magnetic field is received by individual coil blocks of the receiving antenna 7, and detection results corresponding to magnetic field strengths are captured into the position calculation unit 13 via the receiver unit 12 of the endoscope insertion shape observation apparatus 70.

The scope model and marker shape generation unit 66, which operates similarly to the scope model generation unit 14, connects the position coordinates of the respective transmitter coils 2a, thereby generating a linear image as an insertion shape image, and generates an image (marker image) of a predetermined marker shape around position coordinates of the transmitter coil 71. Output of the scope model and marker shape generation unit 66 is supplied to the display control unit 25. The display control unit 25 is designed to cause the marker image to be displayed on the display screen of the monitor 35 together with the insertion shape image and the compression position display.

The position determination unit 61 detects a manual compression point based on occurrence of insertion difficulty state. Besides, if retraction of the insertion portion 2 is detected after the detection of the manual compression point, the position determination unit 61 calculates a distance between the manual compression point 65 and the transmitter coil 71 using the distance calculation unit 61b. The position determination unit 61 is designed to output a signal for turning off the compression position display to the display control unit 25 via the shape generation unit 23, when the distance between the manual compression point 65 and the transmitter coil 71 becomes larger than a predetermined threshold.

Figure 19:
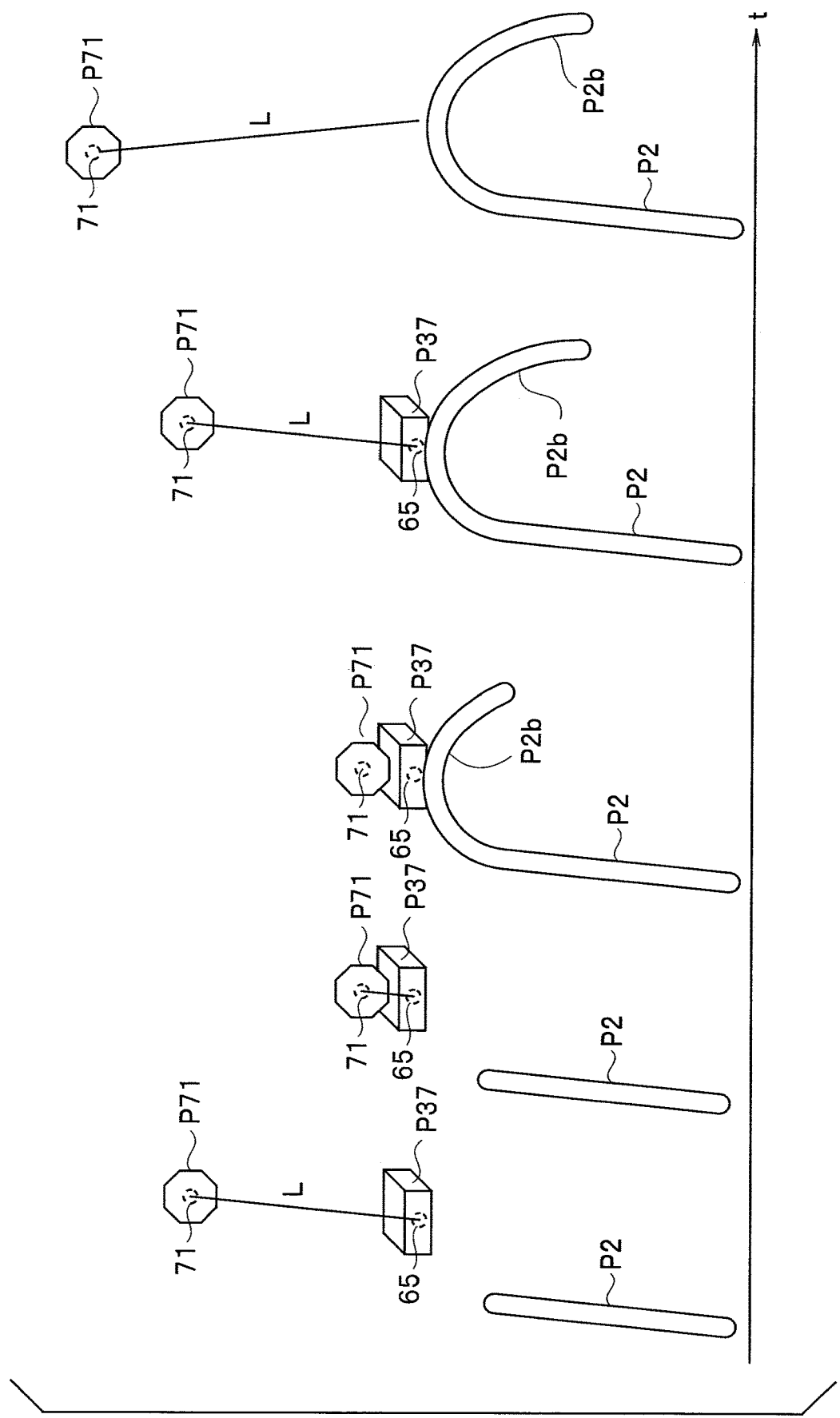
FIG. 19 is an explanatory diagram showing an example of display on the monitor 35 during insertion of the insertion portion 2 in the fifth embodiment, where the display is presented by a display method similar to the display method in FIG. 15.

Next, operation of the embodiment configured in this way will be described with reference to FIG. 19. FIG. 19 is an explanatory diagram showing an example of display on the monitor 35 during insertion of the insertion portion 2, where the display is presented by a display method similar to the display method in FIG. 15.

As with the third display example of FIG. 15 from the left, the first display example of FIG. 19 from the left shows that occurrence of "insertion difficulty state" has resulted in retraction of the insertion portion 2. It is assumed that the in-vitro marker 67 is attached to a hand of the caregiver by a non-illustrated fastener. A position of the in-vitro marker 67 is detected by the position calculation unit 13 based on a signal from the receiving antenna 7. The scope model and marker shape generation unit 66 generates a marker image of a predetermined shape including the position of the in-vitro marker 67 detected by the position calculation unit 13. The marker image is given to the display control unit 25 and is displayed as a marker image P71 on the display screen of the monitor 35 together with the insertion shape image P2 and the compression position display P37 by the display control unit 25.

The position coordinates of the transmitter coil 71 have also been given to the position determination unit 61, and the distance calculation unit 61b calculates the distance L between the manual compression point 65 and the transmitter coil 71. As shown in the first display example of FIG. 19 from the left, at the stage when the insertion portion 2 is retracted, the hand of the caregiver is spaced away from the subject P by the distance L.

By referring to the insertion shape image P2 and the compression position display P37 presented on the monitor 35, the caregiver moves his/her hand to near the manual compression point 65. Note that although not illustrated in FIG. 19, the in-vitro marker 67 moves along with hand movements of the caregiver and a display of the marker image P71 moves as well. When the caregiver places his/her hand near the manual compression point 65, the marker image P71 is displayed at a position adjoining the compression position display P37 as shown in the second display example of FIG. 19 from the left.

In this state, the surgeon reinserts the insertion portion 2. The third display example of FIG. 19 from the left shows how the bending portion 2b passes near the manual compression point 65 as a result of the reinsertion. By confirming this situation, the caregiver takes his/her hand off the body of the subject P. The fourth display example of FIG. 19 from the left shows this state, where the bending portion 2b is spaced away from the manual compression point 65 by moving ahead smoothly while the marker image P71 is also spaced away from the compression position display P37.

The distance calculation unit 61*b* continues calculating the distance L between the manual compression point 65 and the transmitter coil 71, and when the distance L becomes larger than a predetermined threshold, the distance calculation unit 61*b* determines that the compression position display P37 is no longer necessary and outputs a signal for turning off the compression position display P37 to the display control unit 25 via the shape generation unit 23. Consequently, the display control unit 25 turns off display of the compression position display P37. The fifth display example of FIG. 19 from the left shows this state, where the compression position display P37 remains hidden.

In this way, the present embodiment is designed to present not only a compression position display that indicates a manual compression point, but also a marker image that indicates hand movements of the caregiver, making it possible to effectively assist the caregiver in carrying out manual compression procedures. After reinsertion is performed smoothly, the unnecessary compression position display can be turned off.

The present invention is not limited to any of the precise embodiments described above, and may be embodied by changing components in the implementation stage without departing from the gist of the invention. The invention can also be implemented in various forms using appropriate combinations of the components disclosed in the above embodiments. For example, some of the components disclosed in the embodiments may be deleted. Furthermore, components may be combined as appropriate across different embodiments.

What is claimed is:

1. An endoscope insertion shape observation apparatus comprising a processor configured to:
   detect a travelling direction of a first position detection member and a travelling direction of a second position detection member out of a plurality of position detection members provided in an insertion portion inserted into a lumen of a subject, the first position detection member being provided on a distal end side of a bending portion of the insertion portion, the second position detection member being provided on a proximal end side of the bending portion, based on a calculation result from a position calculation circuit that receives signals from the first position detection member and the second position detection member, and based on the received signals, successively calculate position coordinates of the first position detection member and the second position detection member;
   detect a shape of the insertion portion based on a calculation result from the position calculation circuit that successively calculates respective position coordinates of the plurality of position detection members based on signals received from the plurality of position detection members;
   detect that a shape of the insertion portion becomes a predetermined shape, to start detecting a stretch start timing in which the lumen starts stretching;
   detect the stretch start timing in which the lumen starts stretching, based on a change in the travelling direction of the first position detection member with respect to the travelling direction of the second position detection member and find position coordinates of a predetermined position of the bending portion in the stretch start timing as a manual compression point, with a calculation result for the plurality of position detection members from the position calculation circuit; and
   cause a compression position display that indicates the predetermined position found as the manual compression point to be presented on a monitor.

2. The endoscope insertion shape observation apparatus according to claim 1, wherein the processor is configured to designate a position where a curvature of the bending portion is largest in the stretch start timing as the predetermined position, to designate position coordinates of the predetermined position as the manual compression point.

3. The endoscope insertion shape observation apparatus according to claim 2, wherein the processor is configured to find the manual compression point using position coordinates of the plurality of position detection members provided in the bending portion.

4. The endoscope insertion shape observation apparatus according to claim 1, wherein the processor is configured to calculate velocity vectors of the first and second position detection members.

5. The endoscope insertion shape observation apparatus according to claim 1, wherein the processor is configured to start detecting the stretch start timing when an average value of curvatures of various parts of the bending portion is larger than a predetermined threshold.

6. The endoscope insertion shape observation apparatus according to claim 1, wherein the processor is configured to start detecting the stretch start timing when the insertion portion assumes a stick-like shape, a distal end side of which is bent and a proximal end side of which is substantially linear.

7. The endoscope insertion shape observation apparatus according to claim 1, wherein the processor is configured to generate a model of an insertion shape image that indicates a shape of the insertion portion inserted into the lumen, based on position coordinates of the plurality of position detection members that are obtained by the position calculation circuit, and cause the insertion shape image and the compression position display to be presented simultaneously on the monitor.

8. The endoscope insertion shape observation apparatus according to claim 7, wherein the processor is configured to read, from a memory, display data of an external body shape image of an external shape of the subject, and generate a model of the external body shape image and cause the insertion shape image, the compression position display, and the external body shape image to be presented simultaneously on the monitor.

9. The endoscope insertion shape observation apparatus according to claim 7, wherein the processor is configured to calculate a distance between the manual compression point and the first position detection member and turn off display of the compression position display if the first position detection member is spaced away from the manual compression point by a distance equal to or larger than a predetermined threshold after the insertion portion gets close to the manual compression point as a result of reinsertion after having been retracted from the lumen after detection of the stretch start timing.

10. The endoscope insertion shape observation apparatus according to claim 7, wherein the processor is configured to calculate a distance between the manual compression point and each of the plurality of position detection members and cause a position of the position detection member located closest to the manual compression point to be displayed in color on the insertion shape image after detection of the stretch start timing.

11. The endoscope insertion shape observation apparatus according to claim 7, wherein the processor is configured to:

calculate a distance between the manual compression point and an in-vitro marker;
generate a model of a marker image that indicates a shape of the in-vitro marker, based on position coordinates of the in-vitro marker; and
simultaneously present the compression position display, the insertion shape image, and the marker image on the monitor, and turn off display of the compression position display if the in-vitro marker is spaced away from the manual compression point by a distance equal to or larger than a predetermined threshold after the insertion portion gets close to of the manual compression point as a result of reinsertion after having been retracted from the lumen after detection of the stretch start timing.

12. A manual compression position display method comprising:
detecting a travelling direction of a first position detection member and a travelling direction of a second position detection member out of a plurality of position detection members provided in an insertion portion inserted into a lumen of a subject, the first position detection member being provided on a distal end side of a bending portion of the insertion portion, the second position detection member being provided on a proximal end side of the bending portion, based on a calculation result from a position calculation circuit that receives signals from the first position detection member and the second position detection member, and based on the received signals, successively calculate position coordinates of the first position detection member and the second position detection member;
detecting a shape of the insertion portion based on a calculation result from the position calculation circuit that successively calculates respective position coordinates of the plurality of position detection members based on signals received from the plurality of position detection members;
detecting that a shape of the insertion portion becomes a predetermined shape, to start detecting a stretch start timing in which the lumen starts stretching;
detecting the stretch start timing in which the lumen starts stretching, based on a change in the travelling direction of the first position detection member with respect to the travelling direction of the second position detection member;
calculating position coordinates of a predetermined position of the bending portion in the detected stretch start timing as a manual compression point, with a calculation result for the plurality of position detection members from the position calculation circuit; and
causing a compression position display that indicates the predetermined position calculated as the manual compression point to be presented on a monitor.

* * * * *